United States Patent
Bouton et al.

(10) Patent No.: US 12,343,521 B2
(45) Date of Patent: *Jul. 1, 2025

(54) NEURAL SLEEVE FOR NEUROMUSCULAR STIMULATION, SENSING AND RECORDING

(71) Applicant: Battelle Memorial Institute, Columbus, OH (US)

(72) Inventors: Chad E. Bouton, Powell, OH (US); Jeffrey Friend, Columbus, OH (US); Gaurav Sharma, Lewis Center, OH (US); Andrew Sweeney, Columbus, OH (US); Amy M. Heintz, Dublin, OH (US); Stephanie Kute, Columbus, OH (US); Nicholas Annetta, Columbus, OH (US); Thomas D Haubert, Columbus, OH (US); Steven M. Risser, Reynoldsburg, OH (US); Alexander Morrow, Gahanna, OH (US); Raymond Richard Zaborski, Westerville, OH (US); George Naegele Brand, Dublin, OH (US); Matthew Edward Mowrer, Saint Clairsville, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/413,464

(22) Filed: Jan. 16, 2024

(65) Prior Publication Data

US 2024/0207605 A1    Jun. 27, 2024

Related U.S. Application Data

(60) Division of application No. 15/872,734, filed on Jan. 16, 2018, now abandoned, which is a continuation of
(Continued)

(51) Int. Cl.
*A61N 1/04* (2006.01)
*A61N 1/36* (2006.01)
*G06F 3/01* (2006.01)

(52) U.S. Cl.
CPC .......... *A61N 1/0484* (2013.01); *A61N 1/0456* (2013.01); *A61N 1/36003* (2013.01); *G06F 3/015* (2013.01); *G06F 3/017* (2013.01)

(58) Field of Classification Search
CPC .............. A61N 1/0551; A61N 1/36003; A61N 1/0452; A61N 1/0456; A61N 1/0472;
(Continued)

(56) References Cited

U.S. PATENT DOCUMENTS

| 3,845,771 A | 11/1974 | Vise |
| 6,341,237 B1 | 1/2002 | Hurtado |

(Continued)

FOREIGN PATENT DOCUMENTS

| EP | 1928218 B1 | 4/2021 |
| WO | WO 2009038835 A1 | 3/2009 |

(Continued)

OTHER PUBLICATIONS

"FDA approves BrainsGate stroke treatment study", Jul. 26, 2012, Globes' correspondent, downloaded from http://www.globes.co.il/serveen/globes/docview.asp?did=1000769176&fid=1725.
(Continued)

*Primary Examiner* — Deborah L Malamud
(74) *Attorney, Agent, or Firm* — Lippes Mathias LLP

(57) ABSTRACT

The present disclosure relates to neuromuscular stimulation and sensing cuffs. The neuromuscular stimulation cuff has at least two fingers and a plurality of electrodes disposed on each finger. More generally, the neuromuscular stimulation cuff includes an outer, reusable component and an inner, disposable component. One or more electrodes are housed (Continued)

within the reusable component. The neuromuscular stimulation cuff may be produced by providing an insulating substrate layer, forming a conductive circuit on the substrate layer to form a conductive circuit layer, adhering a cover layer onto the conductive circuit layer to form a flexible circuit, and cutting at least one flexible finger from the flexible circuit. The neuromuscular stimulation cuff employs a flexible multi-electrode design which allows for reanimation of complex muscle movements in a patient, including individual finger movement.

5 Claims, 28 Drawing Sheets

Related U.S. Application Data application No. 14/728,512, filed on Jun. 2, 2015, now Pat. No. 9,884,179, which is a continuation-in-part of application No. 14/649,025, filed as application No. PCT/US2013/073247 on Dec. 5, 2013, now Pat. No. 9,884,178.

(60) Provisional application No. 61/734,150, filed on Dec. 6, 2012, provisional application No. 61/733,736, filed on Dec. 5, 2012.

(58) Field of Classification Search
CPC .... A61N 1/0476; A61N 1/0492; A61N 1/375; A61N 1/3758; Y10S 439/909
See application file for complete search history.

(56) References Cited

U.S. PATENT DOCUMENTS

| | | |
|---|---|---|
| 6,609,018 B2 | 8/2003 | Cory |
| 10,765,859 B2 * | 9/2020 | Bouton .................. A61B 5/686 |
| 2004/0249302 A1 | 12/2004 | Donoghue et al. |
| 2006/0253167 A1 | 11/2006 | Kurtz et al. |
| 2008/0215128 A1 | 9/2008 | Rainey et al. |
| 2008/0288020 A1 | 11/2008 | Einav et al. |
| 2009/0082646 A1 | 3/2009 | Bouton |
| 2010/0076533 A1 | 3/2010 | Dar et al. |
| 2010/0198044 A1 | 8/2010 | Gehman |
| 2011/0021943 A1 | 1/2011 | Lacour et al. |
| 2011/0054286 A1 | 3/2011 | Crosby |
| 2011/0237921 A1 | 9/2011 | Askin, III et al. |
| 2012/0316624 A1 | 12/2012 | Smith |

FOREIGN PATENT DOCUMENTS

| | | |
|---|---|---|
| WO | WO 2012/139124 A1 | 10/2012 |
| WO | WO 2012/143850 A1 | 10/2012 |
| WO | WO 2012/155917 A2 | 11/2012 |

OTHER PUBLICATIONS

Garrett et al., "Problem 6: Neural Decoding and Modulation in Patients with Tetraplegia", Presentation by Chad Bouton of Battelle Memorial Institute.

Humber et al., "Nonsmooth Formulation of the Support Vector Machine for a Neural Decoding Problem", arXiv: 1012.0958v1 [math.OC] Dec. 5, 2010.

Pasley et al., "Reconstructing Speech from Human Auditory Cortex", PLoS Biology, www.plosbiology.org, Jan. 2012, vol. 10, Issue 1, e1001251.

Sweeney et al., "Neuromuscular stimulation selectivity of multiple-contact nerve cuff electrode arrays", Med. & Biol. Eng. & Comput., 1995, 33, 418-425.

European Search Report of Application No. EP23156397 Dated May 16, 2023.

* cited by examiner

NEURAL SLEEVE FOR NEUROMUSCULAR STIMULATION, SENSING AND RECORDING

CROSS-REFERENCE TO RELATED APPLICATIONS

This application is a divisional of U.S. patent application Ser. No. 15/872,734, which is a continuation of U.S. patent application Ser. No. 14/728,512, filed Jun. 2, 2015, now U.S. Pat. No. 9,884,179, which is a continuation-in-part of U.S. patent application Ser. No. 14/649,025, filed on Jun. 2, 2015, now U.S. Pat. No. 9,884,178, which is a 371 of PCT Application No. PCT/US2013/073247, filed on Dec. 5, 2013, which claimed priority to both U.S. Provisional Patent Application Ser. No. 61/733,736, filed on Dec. 5, 2012, and to U.S. Provisional Patent Application Ser. No. 61/734,150, filed on Dec. 6, 2012.

BACKGROUND

The following relates generally to systems, methods and devices for neuromuscular stimulation, sensing, and recording. Generally, the system may be used to receive thought signals indicative of an intended action and provide electrical stimulation to nerves and/or muscles to effectuate the intended action, thereby bypassing or assisting a damaged or degenerated region/pathway of the nervous system. The devices of the present disclosure are neuromuscular stimulation cuffs, also referred to herein as "neural sleeves," which deliver stimulation to restore movement to parts of the body not under volitional control due to damaged or degenerated neural regions/pathways from brain or spinal cord injury, stroke, nerve damage, motor neural disease, and other conditions or injuries. The system can also be used in a patient that has some local neural or muscle degeneration for therapeutic or rehabilitation purposes.

Subcutaneous implantable neurostimulation cuffs have been commonly used to block pain and to restore function to damaged or degenerative neural pathways. These implantable cuffs are wrapped around a target nerve and generally include one or more electrodes arranged to stimulate the nerve. By including more than one electrode and/or a different geometry of electrodes, implantable cuffs such as the flat interface nerve electrode (FINE) have been able to achieve stimulation selectivity at the level of individual nerve vesicles.

Transcutaneous neurostimulation cuffs behave similarly to implantable cuffs, however there are important differences. Because the electrodes are placed on the surface of the skin, rather than below it, stimulation often can better target skeletal muscle tissue or muscle groups, rather than peripheral nerves located deeper under the skin. Muscular stimulation may be preferable to stimulating major peripheral nerves, e.g. ulnar, median, radial nerves, as stimulating these nerves may cause a patient to feel a tingling sensation and it is more difficult to effect the desired movement. By increasing the number and layout of electrodes in a neuromuscular cuff, similar to the direction taken with implanted nerve cuff designs, current generation neuromuscular stimulation cuffs have been able to selectively stimulate individual muscles or muscle groups and achieve finer movements such as individual finger flexing and extension.

Flexible-like transcutaneous cuffs have been developed which fit around a human appendage such as a forearm to control the wrist or fingers. These flexible cuffs may include sensors which record muscle activity, or electromyography (EMG) signals, and stimulate in response to the EMG signals. Thin film technologies have also become important in the development of functional electrostimulation (FES) devices. Devices incorporating thin film technology are often based on a polyimide substrate covered by a chromium, gold, or platinum film.

Current transcutaneous neuromuscular stimulation electrodes (or patches) present many limitations. Such neuromuscular patches are typically large (several cm across or more) and have a single electrode (conductive surface). This does not allow selective stimulation of small muscles segments for fine wrist and finger control.

It would be desirable to provide improved devices for neuromuscular stimulation. Flexible sleeves with multiple small electrodes would allow programmable spatial stimulation patterns, which is highly desirable when attempting to restore complex muscular movements through neuromuscular stimulation.

BRIEF DESCRIPTION

The present disclosure relates to systems, methods, and devices for thought-controlled neuromuscular stimulation. Included is a neuromuscular stimulation cuff (i.e. "neural sleeve") which receives a thought signal indicative of an intended action, and in response, stimulates a damaged region/pathway of the nervous system to effectuate the intended action. The neuromuscular cuff may include a flexible design, e.g., including a plurality of electrodes arranged on flexible fingers. The flexible fingers allow for variable sized neuromuscular regions, e.g. paralyzed limbs, to fit within the neuromuscular cuff. The fingers may also allow for increased electrode positioning choices for reanimation of complex muscle movements. The neuromuscular cuff may further include an array of electrogel discs which provide enhanced electrical contact as well as keep the cuff adhered to the skin during stimulation-induced movement.

In yet other embodiments, a device for neuromuscular stimulation includes a flexible printed circuit board having at least one finger and a plurality of electrogel discs disposed on the at least one finger.

In additional different embodiments, a method for producing a neuromuscular cuff includes providing a layer of polyimide, etching a conductive copper circuit including a plurality of electrodes into the layer of polyimide to form an etched circuit layer, adhering a cover layer onto the etched circuit layer to form a flexible printed circuit board (PCB), and cutting at least one finger from the flexible PCB.

In other embodiments disclosed herein, devices for neuromuscular stimulation include: a reusable sleeve; and one or more electrodes housed within the reusable sleeve.

In particular embodiments, the reusable sleeve comprises at least two flexible fingers along which the one or more electrodes are located, each flexible finger extending in the same direction from a connector. Each finger contains one or more flexible conductive pathways that lead to the electrode(s) previously described. A plurality of conductive mediums is disposed on the flexible fingers to conduct the electrical impulses from the electrodes. As a result, each flexible finger is able to conform to different arm profiles and accommodate twisting of the arm.

The conductive medium may comprise a hydrogel, a lotion, or a conductive polymer. The flexible fingers may be oriented with respect to the connector so that they can be wrapped helically (e.g. around a patient's limb). The device may further comprise a fabric layer disposed on an exterior of the reusable sleeve.

Each flexible finger may include a conductive circuit layer, which can be arranged in the form of one or more conductive pathways. That conductive circuit layer may be laid upon an insulating base layer, for example made of a polyimide. The flexible finger may include an insulating cover layer over the conductive circuit layer. The flexible finger may include a plurality of hydrogel discs disposed over each electrode, wherein each hydrogel disk is independently connected to a rigidizer. The rigidizer may interface with a processing device, such as a computer or other electronic device.

In other embodiments, a device for neuromuscular stimulation includes: a reusable sleeve; multiple electrodes housed within the reusable sleeve; and an inner disposable sleeve, the inner disposable sleeve comprising a conductive medium in contact with the multiple electrodes.

The conductive medium may comprise a hydrogel which is relatively more conductive in a z-direction than in a x-direction or a y-direction. The conductive medium may be less conductive in a regular state; and the conductive medium may become more conductive upon application of external pressure in a direction of the external pressure. The conductive medium may include a compressible polymer and a conductive filler dispersed in the compressible polymer. The conductive filler may be carbon-based and comprise carbon fibers. The conductive filler may comprise any of: carbon fibers, carbon nanotubes, or metallic particles (e.g. silver; gold; platinum; or palladium). The conductive medium may be dry in an initial state and then become tacky upon any one of: application of an electrical current; a change in temperature; a change in pH; or a change in moisture. The conductive medium may include a stimuli-sensitive polymer. Each electrode of the multiple electrodes may include concentric rows of teeth about 200 μm to about 300 μm in height. The reusable sleeve may include a flexible material.

In other embodiments, the reusable sleeve may include: a rigid shell; and a hinge running parallel to a longitudinal axis of the reusable sleeve. Sometimes, the reusable sleeve may include a user interface for selectively configuring electrodes and adjusting stimulation level or pattern. The reusable sleeve may be expandable.

In other embodiments, the reusable sleeve may include a compression sleeve fabric on which the multiple electrodes are printed using silk-screen technology employing conductive polycellulose or silver/carbon-based ink. The device may further include a conductive pathway including an accelerometer.

The reusable sleeve may include a flexible circuit which may include electrodes connected by electrode traces; the electrode traces may house sensors; and the electrode traces may be arranged in a zig-zag pattern to enhance flexibility and/or durability. The sensors may include any combination of pressure sensors; strain gauges; accelerometers; a micro-electro-mechanical system (MEMS) including a 3-axis accelerometer and 3-axis magnetometer; a capacitive sensor including a flexible insulating dielectric layer sandwiched between flexible electrodes; a stretch sensor including a material that changes electrical resistance when stretched or strained; a resonant bend sensor including a resistance-inductance-capacitance (RLC) circuit; a sensor including at least one bladder configured to hold a fluid or air; a fiber optic cable and a measurement tool configured to measure a bend in the fiber optic cable based on a frequency or attenuation change in a signal of the fiber optic cable; and a video motion tracking system configured to track a marker of the reusable sleeve.

The reusable sleeve may include conductive/carbon fibers and a dry fit material. The reusable sleeve may be in the form of a fingerless glove made of a stretchy material. The multiple electrodes may be woven into the reusable sleeve using conductive threads. The reusable sleeve may include buttons including light emitting diode (LED) based touch-screen displays on a back side of each of the multiple electrodes. The reusable sleeve may include an accelerometer, and may be configured for gesture control of devices. The reusable sleeve may be configured to cover both a leg portion and a foot portion of a patient; and support gait-training. The reusable sleeve may include a shirt configured to deliver electrical stimulation to a backside of a patient. The multiple electrodes may be configured to both deliver electrical simulation and sense a neural signal of a patient.

In another aspect, a device for neuromuscular stimulation may include: a reusable sleeve; and multiple electrodes housed within the reusable sleeve; wherein the reusable sleeve comprises at least two flexible fingers for housing the multiple electrodes, the flexible fingers extending in the same direction, and a plurality of conductive mediums disposed thereon.

In another aspect, a device for neuromuscular stimulation includes: a reusable sleeve comprising a continuous substrate; and multiple electrodes housed within the reusable sleeve; wherein the continuous substrate comprises a non-conductive portion and conductive, parallel pathways.

These and other non-limiting aspects of the present disclosure are discussed in more detail below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
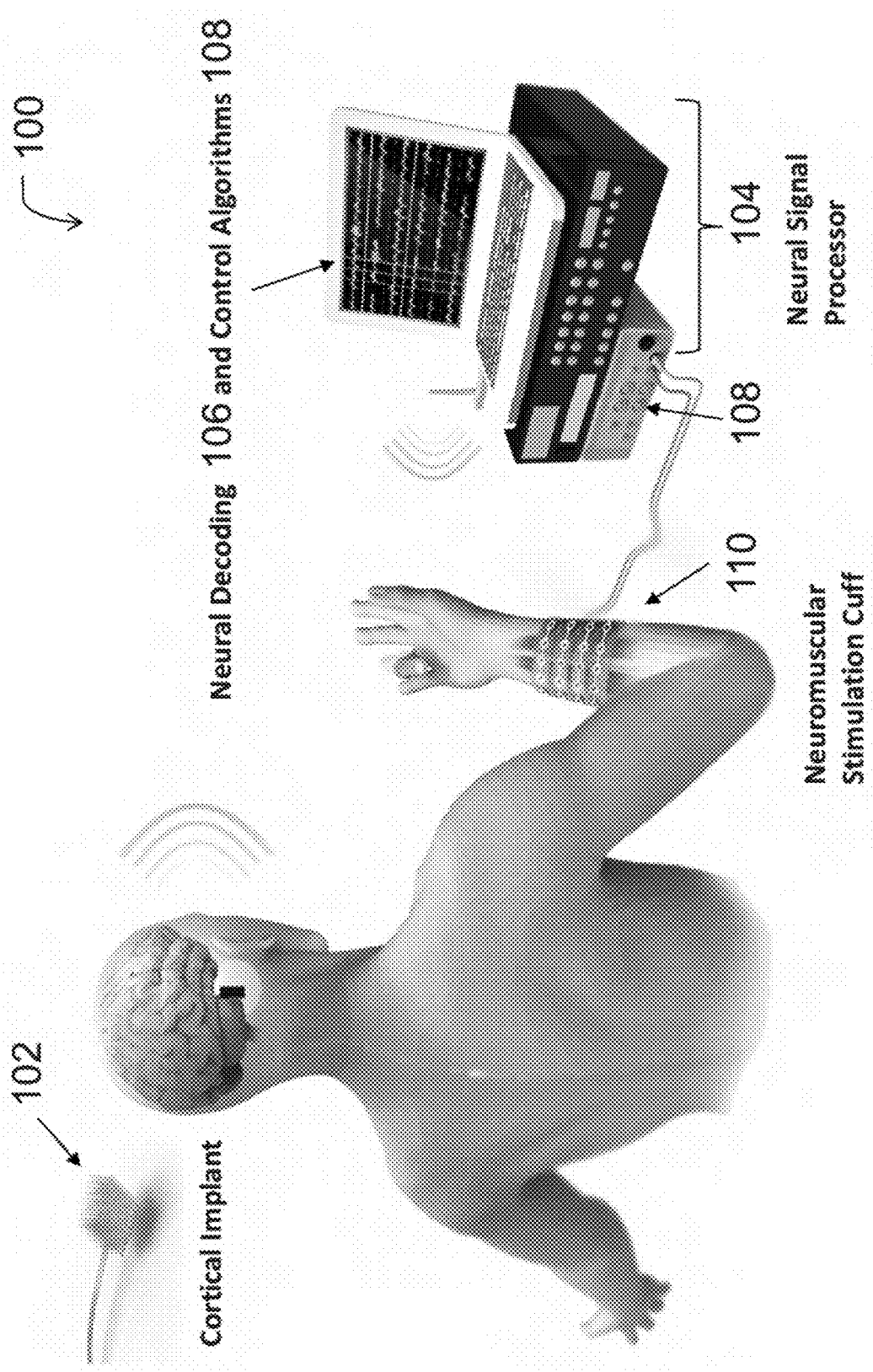
FIG. 1 is an overview diagram of one embodiment of a system for thought-controlled neuromuscular stimulation.

A more complete understanding of the processes and apparatuses disclosed herein can be obtained by reference to the accompanying drawings. These figures are merely schematic representations and are not intended to indicate relative size and dimensions of the assemblies or components thereof.

Although specific terms are used in the following description for the sake of clarity, these terms are intended to refer only to the particular structure of the embodiments selected for illustration in the drawings, and are not intended to limit the scope of the disclosure. In the drawings and the following description below, it is to be understood that like numeric designations refer to components of like function.

Figure 2:
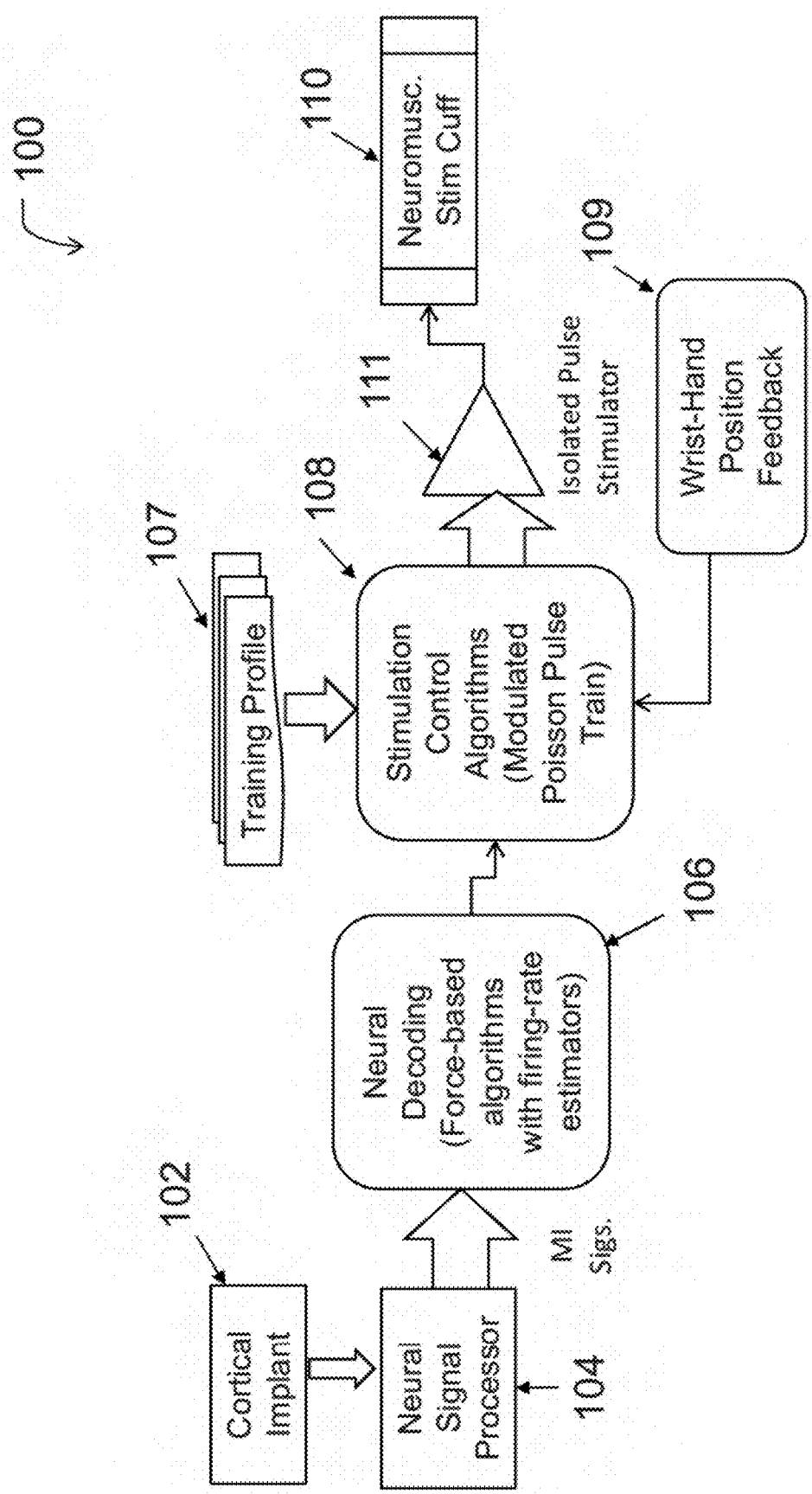
FIG. 2 is a block diagram for the decoding and re-encoding architecture operating within the system of FIG. 1.

With reference to FIG. 1 and FIG. 2, a system for thought-controlled neuromuscular stimulation may include a cortical implant 102 implanted into the cerebral cortex region of the brain. The cortical implant 102 in one embodiment includes a microelectrode sensing array, as depicted in FIG. 1. The microelectrode sensing array includes multiple channels (e.g. 96 channels) and may be wired to an amplifier which further amplifies signals received by the microelectrode array. The cortical implant 102 records "brain waves," more particularly neural signals which are representative of a varied set of mental activities. Neural signals include electrical signals produced by neural activity in the nervous system including action potentials, multi-unit activity, local field potential, ECoG, and EEG. These neural signals are sent wirelessly or, alternatively, through a wired connection, from the cortical implant 102 to a receiver on a neural signal processor device 104 for processing of the neural signals. In another embodiment, a scalp based interface, headset, or other sensor 102 picks up electroencephalogram (EEG) signals and sends them to the receiver on the neural signal processor device 104.

The neural signal processor 104 may include a processor including neural decoding algorithms 106 and/or control algorithms 108. These algorithms 106, 108 allow for a received neural signal input to be decoded and subsequently re-encoded for use in neuromuscular stimulation. For example, a received neural signal may be isolated to predict arm and/or hand movements a patient is thinking about. The neural signal processor 104 may also include an oscilloscope or other signal waveform viewing and/or manipulation device. The neural signal processor also preferably includes an isolated pulse stimulator 111 which receives a processed signal and generates a pulse signal for use in neuromuscular stimulation by an attached neuromuscular stimulation cuff 110.

With reference to FIG. 2, the system for thought control at a more complex architectural level includes the cortical implant or sensor 102 and the neural signal processor 104 which allow for the recording of neural signals and the initial processing of the signals, respectively. Initial signal processing may include analog to digital conversion, normalization, and/or other filtering and processing methods known by one having ordinary skill in the art. Initially processed signals are then decoded by the neural decoding algorithms 106. In exemplary embodiments, the neural decoding algorithms 106 include force-based algorithms with firing-rate estimators.

The decoded signal output of the neural decoding algorithms 106 is further processed by the stimulation control algorithms 108. In exemplary embodiments, the stimulation control algorithms 108 produce an output of peak current amplitude modulated, pulse width modulated, or frequency modulated pulse trains going to the cuff electrodes. The pulse train can also be a non-stationary Poisson type train where average pulse rate (frequency) is modulated. This may help reduce muscle fatigue as it more closely matches to the body's natural nervous system. An example of using poisson-distributed impulse trains to characterize neurons in a region of the brain is disclosed in Pienkowski et al., Wiener-Volterra Characterization of Neurons in Primary Auditory Cortex Using Poisson-Distributed Impulse Train Inputs, J. Neurophysiology (March 2009). Stimulation control algorithms 108 may be altered through input received from a training profile 107. The training profile 107 may include training profile data representative of past user training sessions, e.g. motion demonstrations or coaching periods. Training data may be used to alter and/or define simulation control algorithms 108 during signal processing. Incorporating training data into stimulation control algorithms 108 through a model-based approach yields more accurate decoding, e.g. patient thoughts accurately translated into a complex motion, than prior position-based decoding efforts have shown. Additionally or alternatively, wrist-hand position feedback 109 may be used to alter and/or define stimulation control algorithms 108 during signal processing.

Signal control algorithm 108 output may be sent to the isolated pulse generator 111, where the signal is converted into a waveform that is suitable for neurostimulation. Suitable waveforms may include monophasic and biphasic pulses with a voltage between 80 to 300 Volts. However, even higher voltages may be used as long as safe current levels are maintained and proper insulation is used. In exemplary embodiments, the waveform is a monophasic pulse with a peak current of 0-20 mA which is modulated to vary strength of muscle contraction, frequency of 50 Hz, and a pulse width duration of 500 ms. The output of the isolated pulse generator 111 is sent to the neuromuscular stimulation cuff 110 to deliver functional electrostimulation to the patient.

Figure 3:
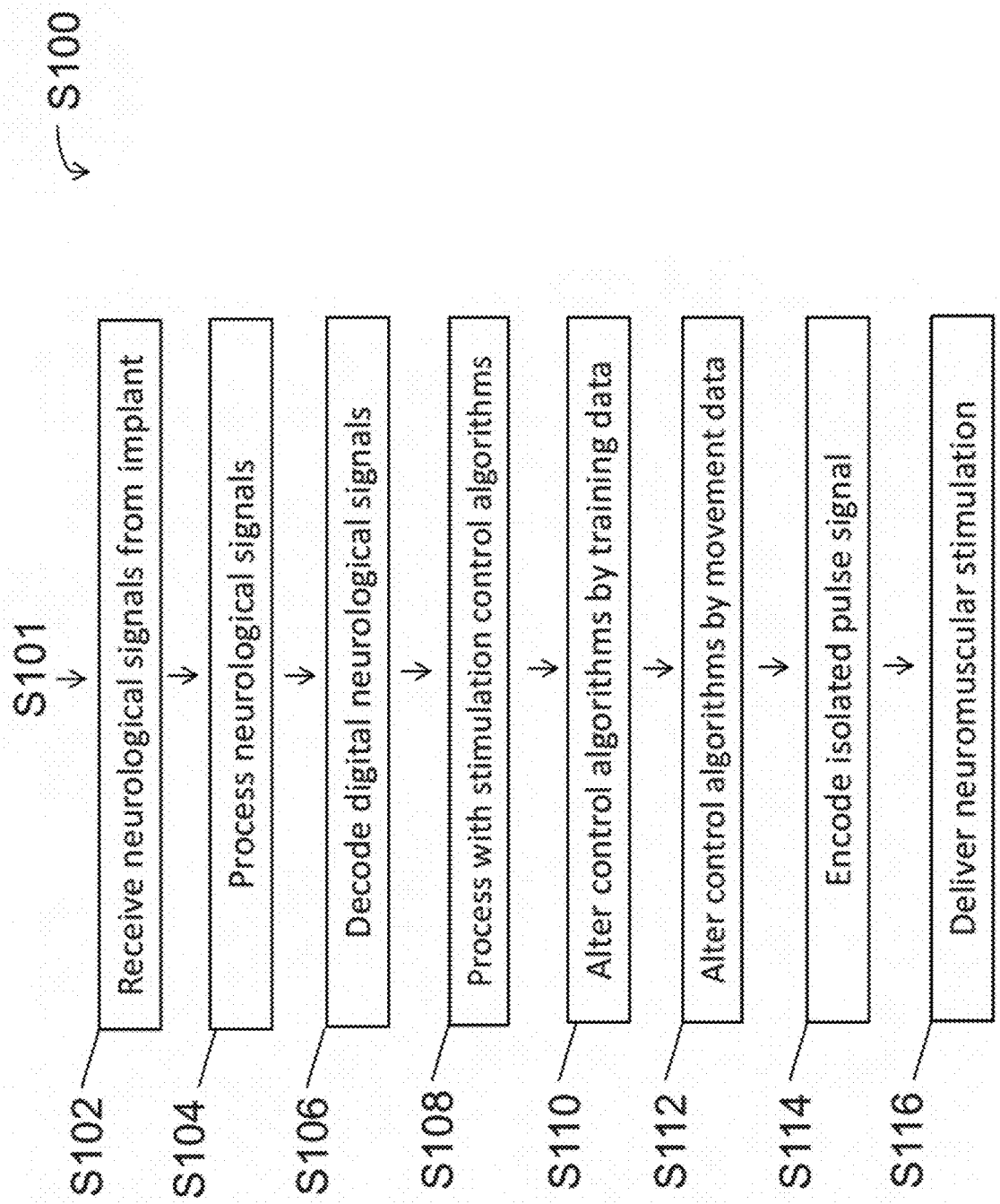
FIG. 3 is a flow diagram for one embodiment of a method for providing thought-controlled neuromuscular stimulation.

With reference to the flow diagram set forth in FIG. 3, a method for providing thought-controlled neuromuscular stimulation S100 starts at S101. At S102 neurological signals are received from a patient indicative of an intended action. For example, neurological signals may be received though cortical implant 102. At S104 the neurological signals are processed, which may include analog to digital conversion or filtering. At S106, the digitized signals are decoded by at least one neural decoding algorithm 106. At S108, the decoded signals are processed by at least one stimulation control algorithm 108. At S110, the method alternatively includes altering the stimulation control algorithms 108 by training data which is stored in the training profile 107. At S112, the method alternatively includes altering the stimulation control algorithms 108 based on movement data, e.g. wrist-hand position feedback 109. At S114, the output of the at least one signal control algorithm 108 is converted into a re-encoded signal consisting of multiple pulse trains, each pulse train going to a corresponding electrode 114. At S114, neuromuscular stimulation is delivered to the patient by sending the re-encoded signal to the neuromuscular stimulation cuff 110.

In another embodiment, the method for providing thought-controlled neuromuscular stimulation S100 further includes at S117 delivering neuromuscular stimulation to the patient by selectively delivering stimulation to at least one pair of electrodes 114 within a neuromuscular cuff 110 to effectuate the intended action.

In yet another embodiment, the method S100 further includes S103 recording neurological signals from a patient. These neurological signals may be sensed from, e.g., a forearm or wrist region with neural pathway damage. Recording may also occur at a neurologically intact region such as a functional leg, for which stimulation pulses can be provided for stimulating commonly tied motions in damaged limbs, e.g. arms and legs. Commonly tied motions include hip and arm movements or pivoting movements. In the same embodiment, method S100 at S118 may further include delivering neuromuscular stimulation to the patient by selectively stimulating to at least one pair of electrodes within the neuromuscular cuff 110 based on the re-encoded signal.

Figure 4:
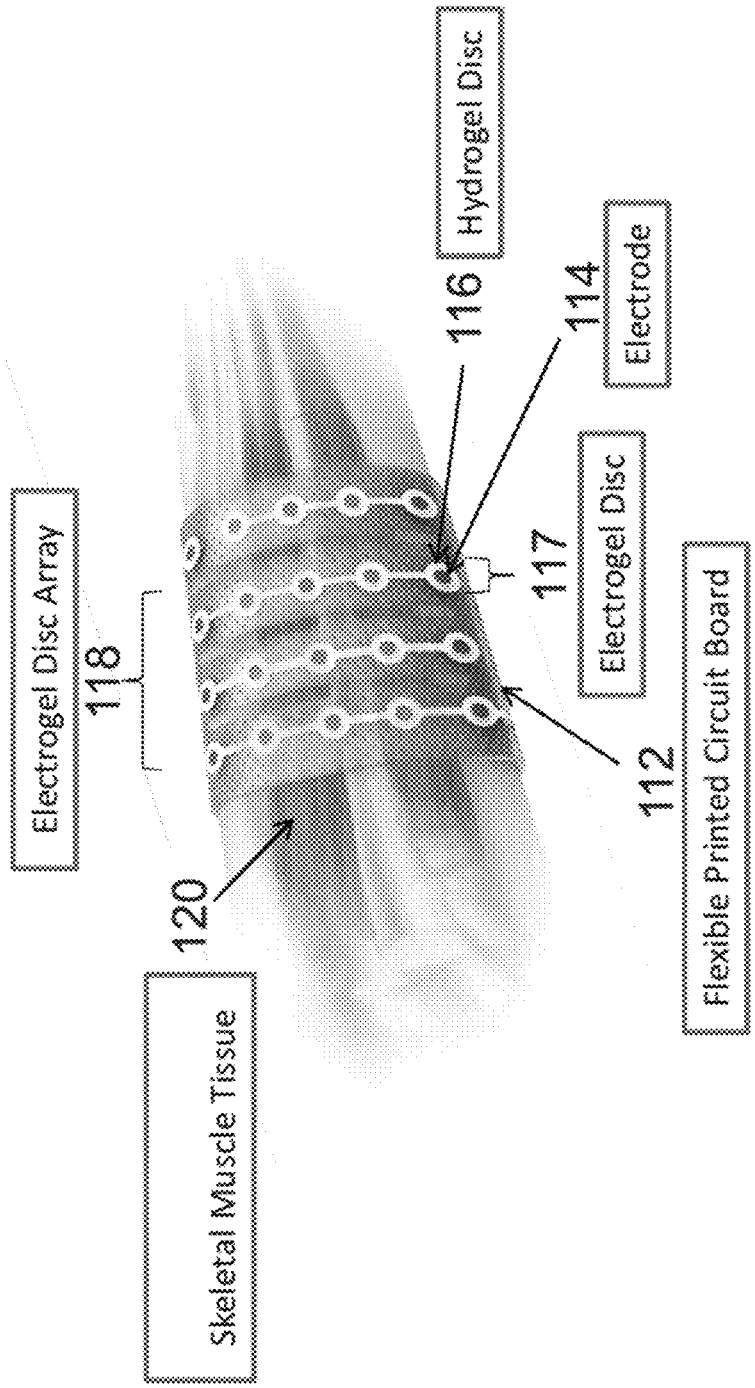
FIG. 4 is a perspective drawing of a neural sleeve according to an exemplary embodiment, shown in place on a human arm.

With reference to FIG. 4, an exemplary embodiment of the neuromuscular stimulation cuff 110 includes a flexible printed circuit board (PCB) 112 upon which electrodes 114 and hydrogel discs 116 are arranged in an electrogel disc array 118. The neuromuscular stimulation cuff 110 fits over a damaged or degenerative region 120 of the nervous system, e.g. a patient's arm as illustrated. The flexible PCB 112 acts as a substrate upon which the electrodes and other conductive materials are laid. This flexible base layer may be comprised of a single layer of a flexible insulating material, for example a polyimide material. Up to approximately twenty electrodes 114 may be individually etched onto each finger 124 of the flexible PCB 112 as a copper layer. In exemplary embodiments, the flexible PCB 112 has a total of eighty electrodes 114 disposed over four fingers 124. The electrodes 114 may be subsequently plated with a conductive metal such as gold, palladium, or silver for greater conductivity.

In some embodiments, electrodes 114 both stimulate a neuromuscular region 120 by stimulating individual muscles and/or groups of muscles, as well as monitor or record skeletal muscle activity, specifically electromyography (EMG) signals. Sensed EMG data pertaining to a sensed muscle target may be used in methods for closed or open loop stimulation of the muscle target. Sensed EMG data may also be analyzed in deciding whether to reposition the neuromuscular stimulation cuff 110 within the neuromuscular region 120 or to turn off individual electrodes 114 within the electrogel disc array 118.

Hydrogel discs 116 may be rolled over the electrodes 114 to provide enhanced electrical and mechanical coupling. When appropriately aligned, the hydrogel discs 116 completely cover the electrodes 114 and effectively form conductive electrogel discs 117. Put another way, the electrodes are located between the base layer and the hydrogel discs. Electrical coupling is enhanced in that hydrogel provides greater conductive contact with the skin than is achievable with a bare metal-plated electrode surface. Additionally, a carrier signal provided to any of the electrogel discs 117 in the electrogel array 118 may conduct through the tissues of a patient and be released at any other electrogel disc 117 provided in the array 118. Enhanced mechanical coupling is provided through the exemplary adherence characteristics of hydrogel to the skin. Hydrogel discs 116 may stay coupled to the skin even during complex patient movement. The hydrogel discs are commercially available as a tape which may be rolled on an electrode surface. One such example includes AmGel 2550 from AmGel Technologies. In the exemplary embodiment of the neuromuscular cuff shown in FIG. 4, the hydrogel discs are provided through custom spaced hydrogel discs located on AmGel 2550 rolled hydrogel tape. In the alternative, instead of hydrogel discs, a lotion or discs of a conductive polymer could be used.

The electrogel disc array 118 is spread over a plurality of fingers 124, wherein the fingers 124 are cut from the flexible PCB 112 to provide additional flexibility in the placement of electrogel discs 117. Reanimation of complex motion may require stimulating muscles which are not located directly along the dimensions of a conventionally shaped neuromuscular cuff 110. By wrapping fingers 124 around different muscular regions, e.g. the lower wrist and thumb, complex motions such as thumb movement may be reanimated more effectively than with limited placement options.

Figure 5:
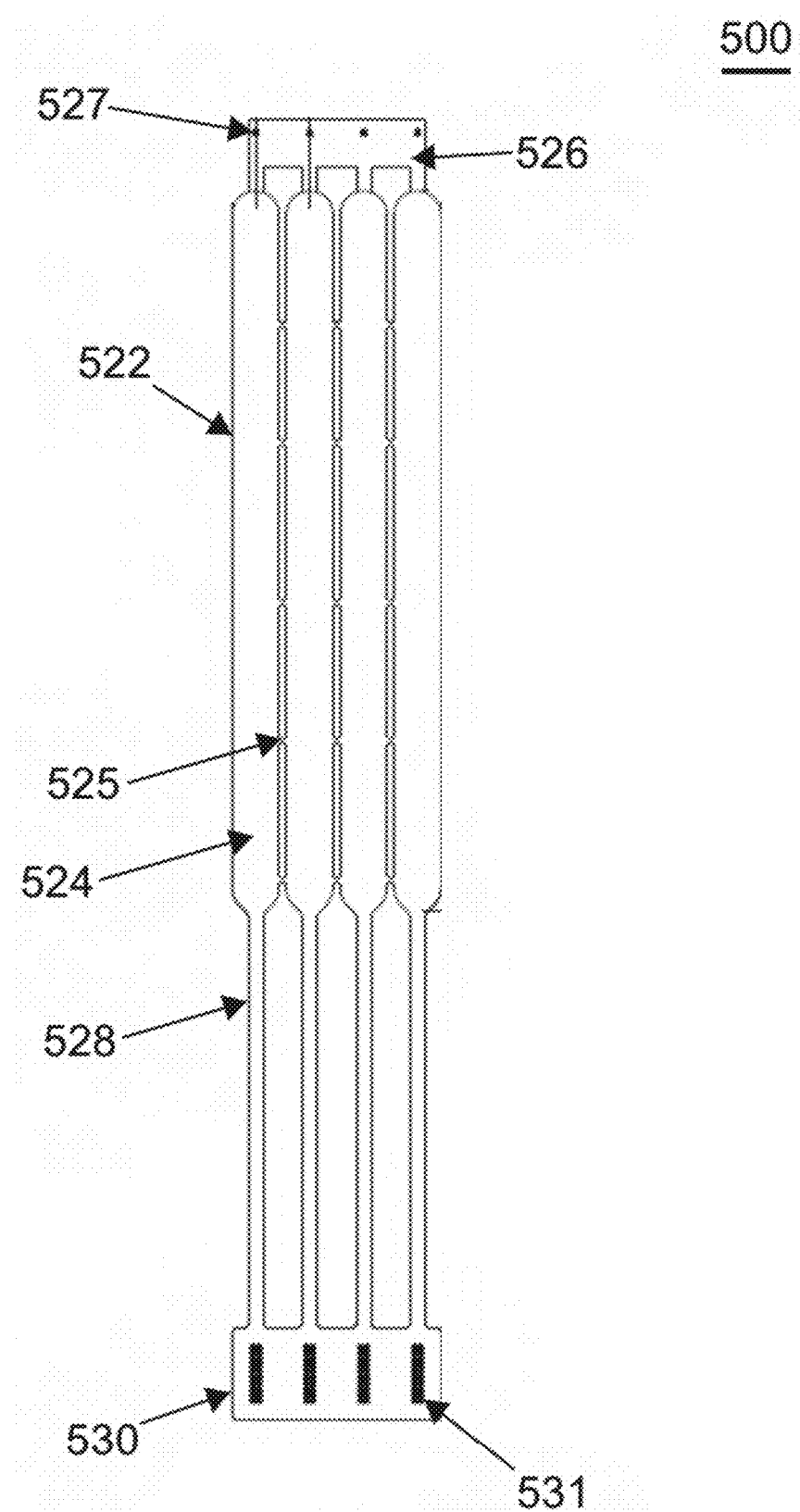
FIG. 5 is a diagram for a concept design for fabricating one embodiment of the neural sleeve.

FIGS. 5-11 are views of various layers of the neuromuscular stimulation cuff, and are separated for convenience and understanding. With reference to FIG. 5, one embodiment of the neuromuscular stimulation cuff device 110 (or neural sleeve) may be fabricated in accordance with a concept design 500. Dimensions of and between the various components of the concept design 500 are indicated in millimeters (mm). The concept design 500 includes, as shown here, an insulating base layer, for example made of a single layer of polyimide base material 522. In some embodiments, the polyimide base material is a DuPont AP8523E polyimide which is 50 μm (micrometers) thick and rolled-annealed copper clad at 18 μm thick. This base material serves as a substrate for the other layers of the neuromuscular stimulation cuff. This base material is formed, for example by cutting, into at least two flexible fingers. As illustrated here, the base material 522 is cut into four fingers 524, where the electrodes will be located or housed. The fingers can be attached to each other, for example by five webbings 525 which run between adjacent fingers.

The fingers 524 extend in the same direction from the rigidizer 530, which acts as a connector for one end of the fingers. In other words, the ends of the fingers distal from the rigidizer are all located in the same direction relative to the rigidizer, or put another way the rigidizer 530 is at one end of the device. It is noted that the fingers 524 are shown here as extending at a 90-degree angle relative to the connector/rigidizer 530. It is contemplated that the flexible fingers could extend at any angle from the connector 530. Referring back to FIG. 4, setting the flexible fingers at an angle from the rigidizer would permit the flexible fingers to be wound helically around the arm and down along the entire length of the arm.

The rigidizer 530 is used for interfacing with the neural signal processor 104. Drilled holes 531 are additionally located on the rigidizer 530 which represent connector pin insertion points. In exemplary embodiments, eighty drilled holes 531 are approximately 1.016 mm in diameter with a tolerance of +/−0.05 mm. As illustrated here, the fingers 524 are parallel to each other along their entire length. As will be seen later, this is not a requirement.

If desired, an optional fork 526 can be located at the end of the fingers opposite the connector/rigidizer 530. The fork connects all of the fingers, and can be provided for structural support for design and mounting. Drilled holes 527 are provided in the fork 526 for support and/or mounting purposes. In some embodiments, the four drilled holes 527 are approximately 2.387 mm in diameter with a tolerance of +/0.076 mm. Headers 528 extend between the rigidizer and the fingers. These headers are thinner than the fingers, and connect the fingers 524 to the rigidizer 530. The headers are also part of the overall flexible finger, though they are not always required. Though not illustrated, webbings can also be provided between adjacent headers as well if desired. Again, as will be seen later, the fork 526 is optional, though the connector 530 is required.

Figure 6:
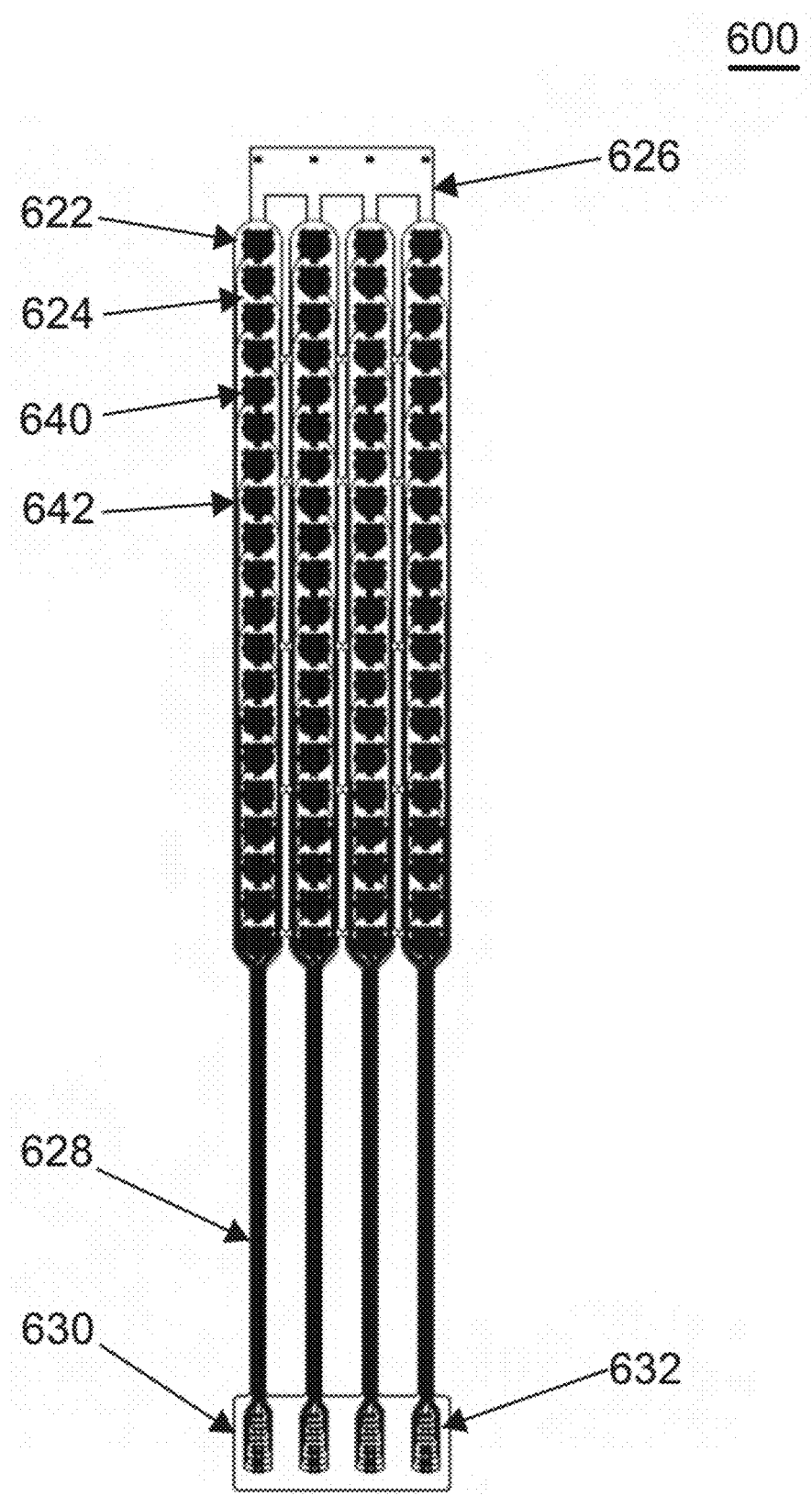
FIG. 6 is a diagram for an etched circuit layer for fabricating one embodiment of the neural sleeve.

With reference to FIG. 6, a conductive circuit layer 600 for fabricating the neuromuscular stimulation cuff device 110 is shown. The conductive circuit layer 600 is located on the surface of the insulating polyimide substrate 622, upon which copper electrodes 640 and connective copper traces 642 are formed to make a conductive pathway, for example by etching, deposition, ablation, etc. The electrodes 640 and traces 642 run along the four fingers 624 of the substrate 622. The traces 642 run longitudinally down the four headers 628 to electrically connect the electrodes 642 to the connector/rigidizer 630. Again, the connector/rigidizer 630 is used for interfacing with the neural signal processor 104. The traces 642 continue onto rigidizer 630 and end, in this exemplary embodiment, at eighty connective points 632, which represents twenty connective points 632 per finger 624. Each of the eighty connective points 632 corresponds to an individual electrode 640, electrically connected through an individual trace 642.

Figure 7:
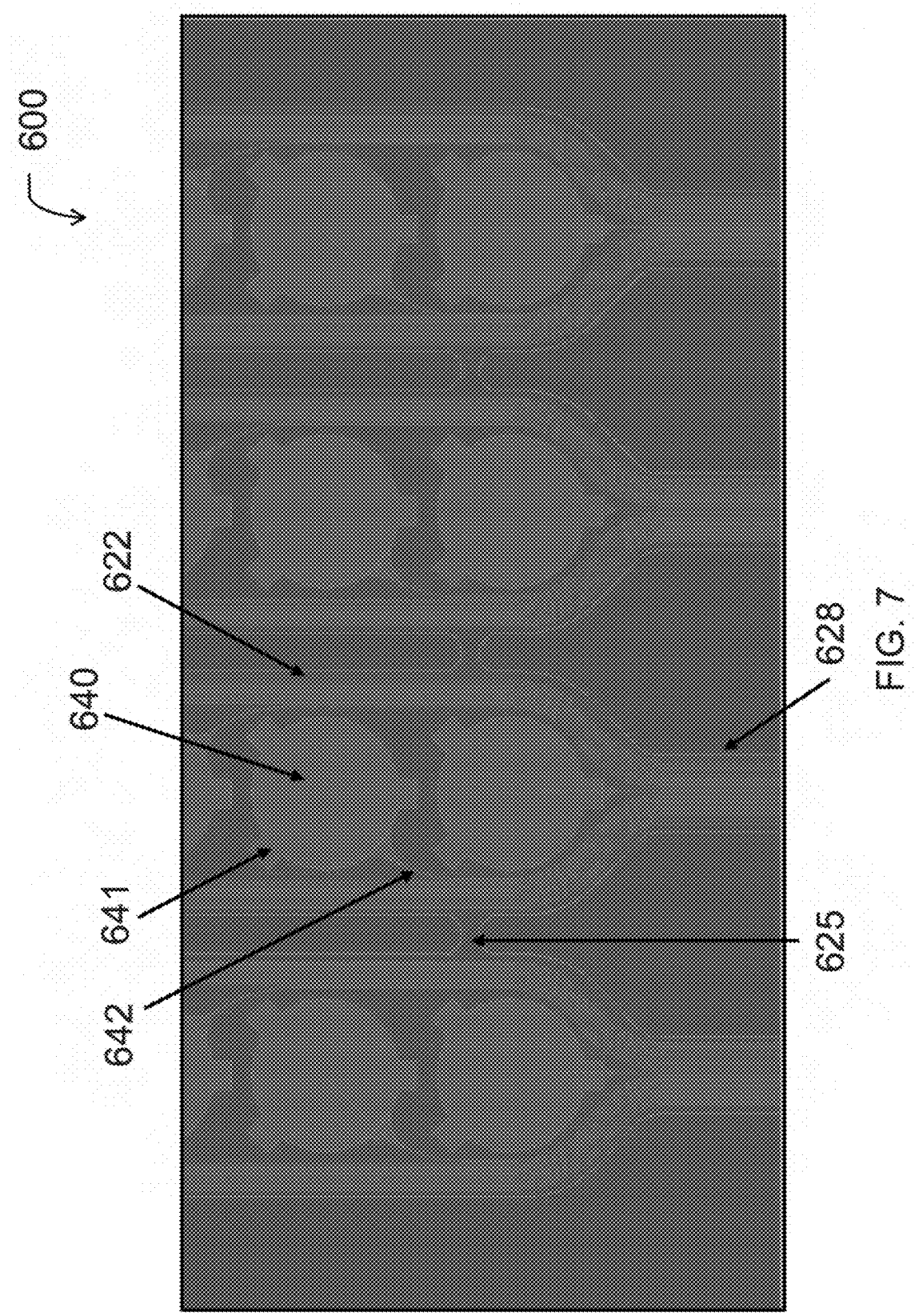
FIG. 7 is a close-up view diagram of the etched circuit layer of FIG. 6.

FIG. 7 is a closer view of the conductive circuit layer 600 of FIG. 6. The substrate 622, electrodes 640, and traces 642 are more particularly seen here. Each electrode 640 is individually connected to a single trace 642, and the trace 642 runs down header 628 to the connector/rigidizer 630 (not shown). In some embodiments, the traces 642 are approximately 0.127 mm in width. As illustrated here, each electrode 640 includes at least one ear 641 which is used to support the electrode 640 upon the insulating substrate 622. As seen here, each electrode includes a central area 643 and three ears 641. The central area has a circular shape, and is used as an electrical contact. Each ear extends beyond the perimeter of the central area. As illustrated here, two ears are separated by 60 degrees, and are separated from the third ear by 150 degrees.

Figure 8:
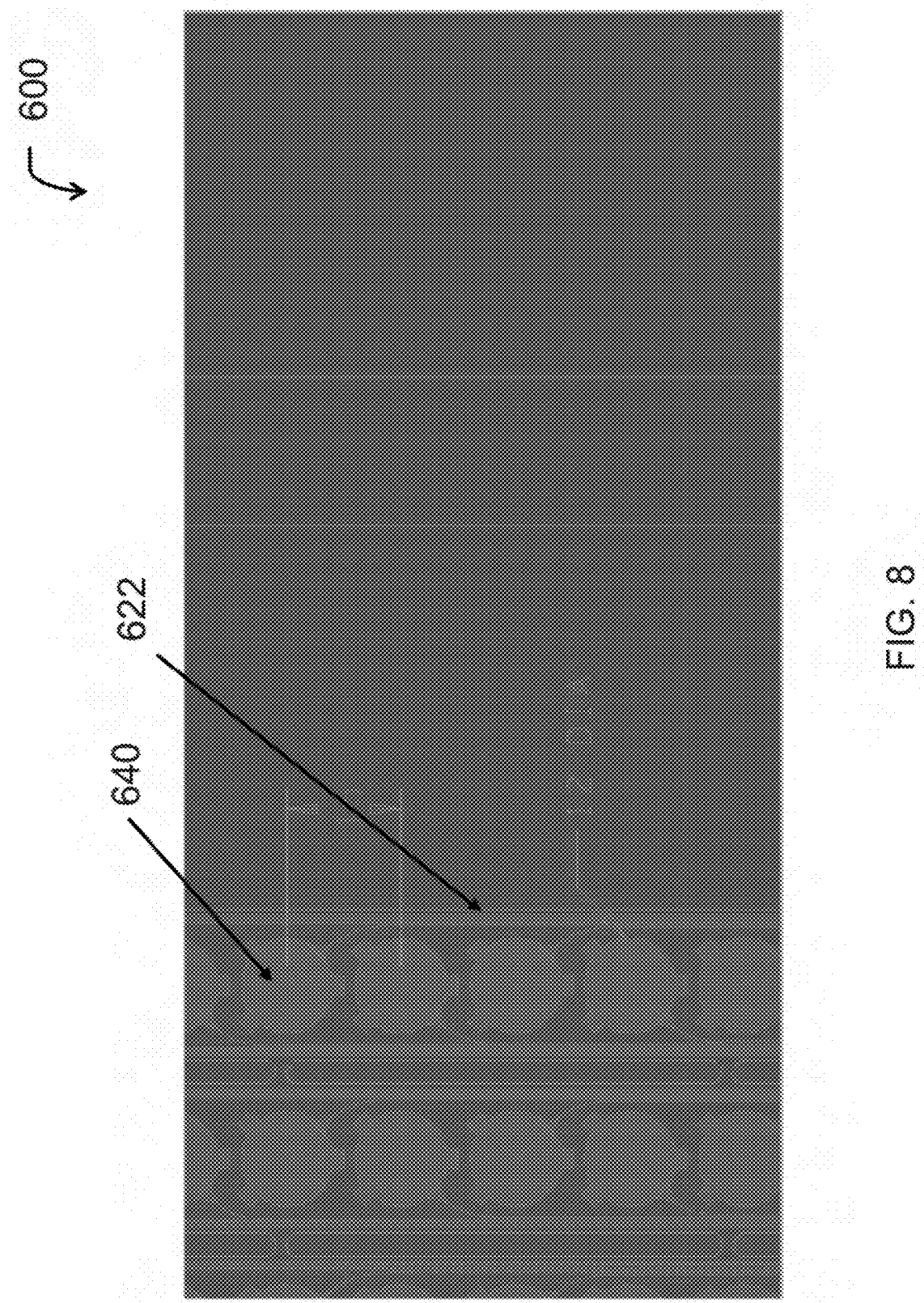
FIG. 8 is an alternative close-up view diagram of the etched circuit layer of FIG. 6.

Referring to FIG. 8, the conductive circuit layer illustrated in FIG. 6 may include electrodes 640 that are approximately 12 mm in diameter (not counting the ear) and spaced 15 mm apart. This 15 mm spacing between electrodes would dictate the custom spacing required for subsequent application of hydrogel discs 114.

Figure 9:
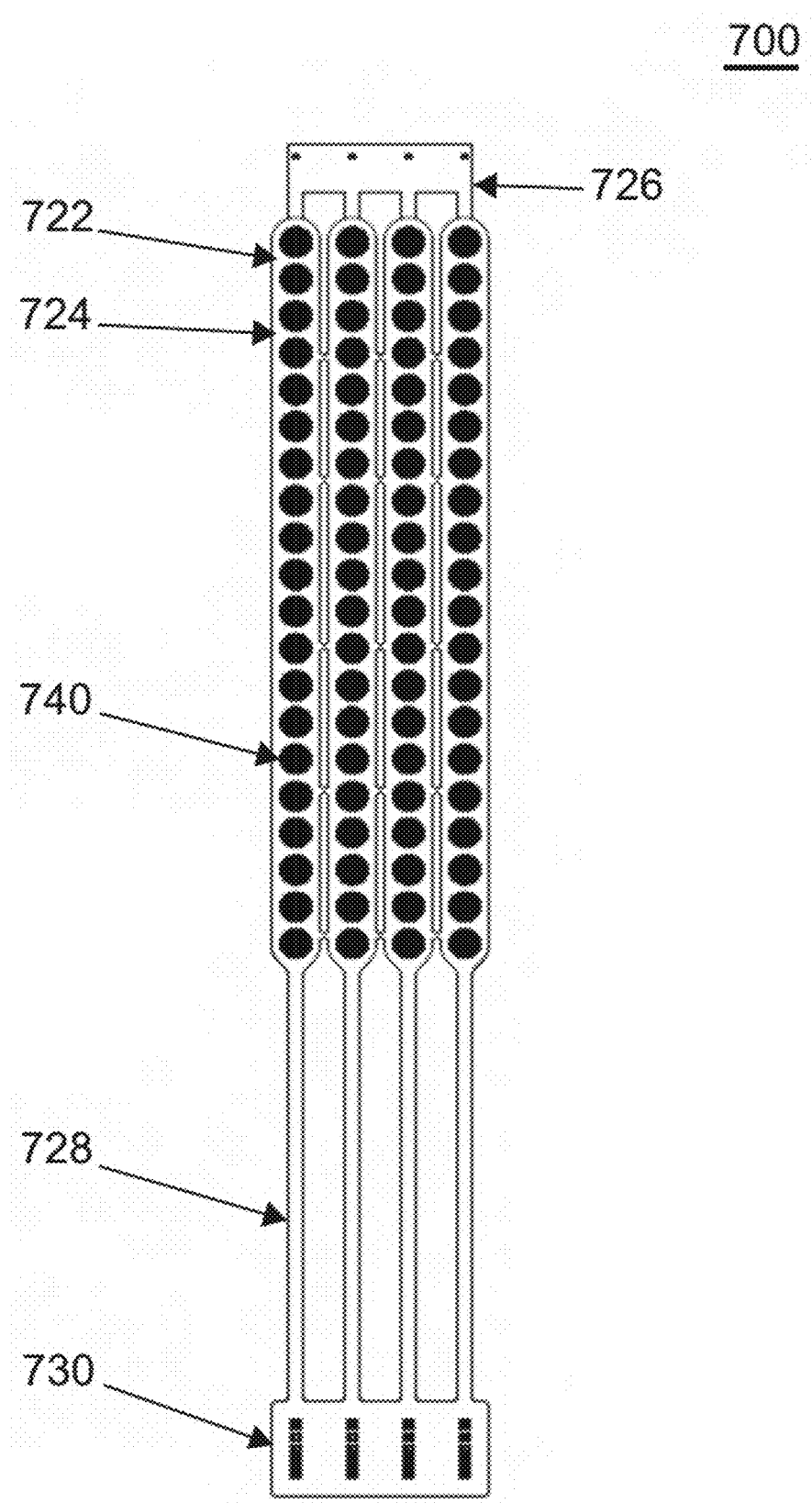
FIG. 9 is a diagram for a coverlay layer used in fabricating one embodiment of the neural sleeve.

FIG. 9 illustrates an insulating cover or "coverlay" layer 700 which would be placed over the electrodes and traces. The coverlay layer can be made from a single layer of an insulating material such as polyimide 722, which is preferably thinner than the substrate upon which the electrodes and traces are copper-etched or otherwise formed. In one embodiment, the coverlay layer is a DuPont LF0110 polyimide material which is a 25 μm thick coverfilm. A further thickness of 25 μm of acrylic adhesive can be used for adhering the coverlay layer 700 to the conductive circuit layer 600. The coverlay layer also includes a fork 726, fingers 724, headers 728, and rigidizer section 730 which corresponds to these areas on the base substrate 522 and the conductive circuit layer 600. Cutouts 740 are left in the fingers to expose the central area of the electrodes, and on the rigidizer section 730 for the electrical connectors.

The insulating cover layer 700, when applied over the conductive circuit layer 600, covers the copper traces 642 formed on the fingers 724 and the headers 728. The coverlay layer 700 does not cover the central area 643 of the electrodes, but does cover the ears 641, thus fixing the electrodes in place between the substrate and the coverlay layer. In addition, the electrical connectors in the rigidizer section 730 will remain uncovered. The exposed central areas of the electrodes 640 are preferably plated with a conductive metal such as tin, platinum, or gold. In one embodiment, exposed copper electrodes are plated with electroless-nickel-immersion-gold (ENIG) at the level of 3-8 μm gold over 100-150 μm nickel.

Figure 10:
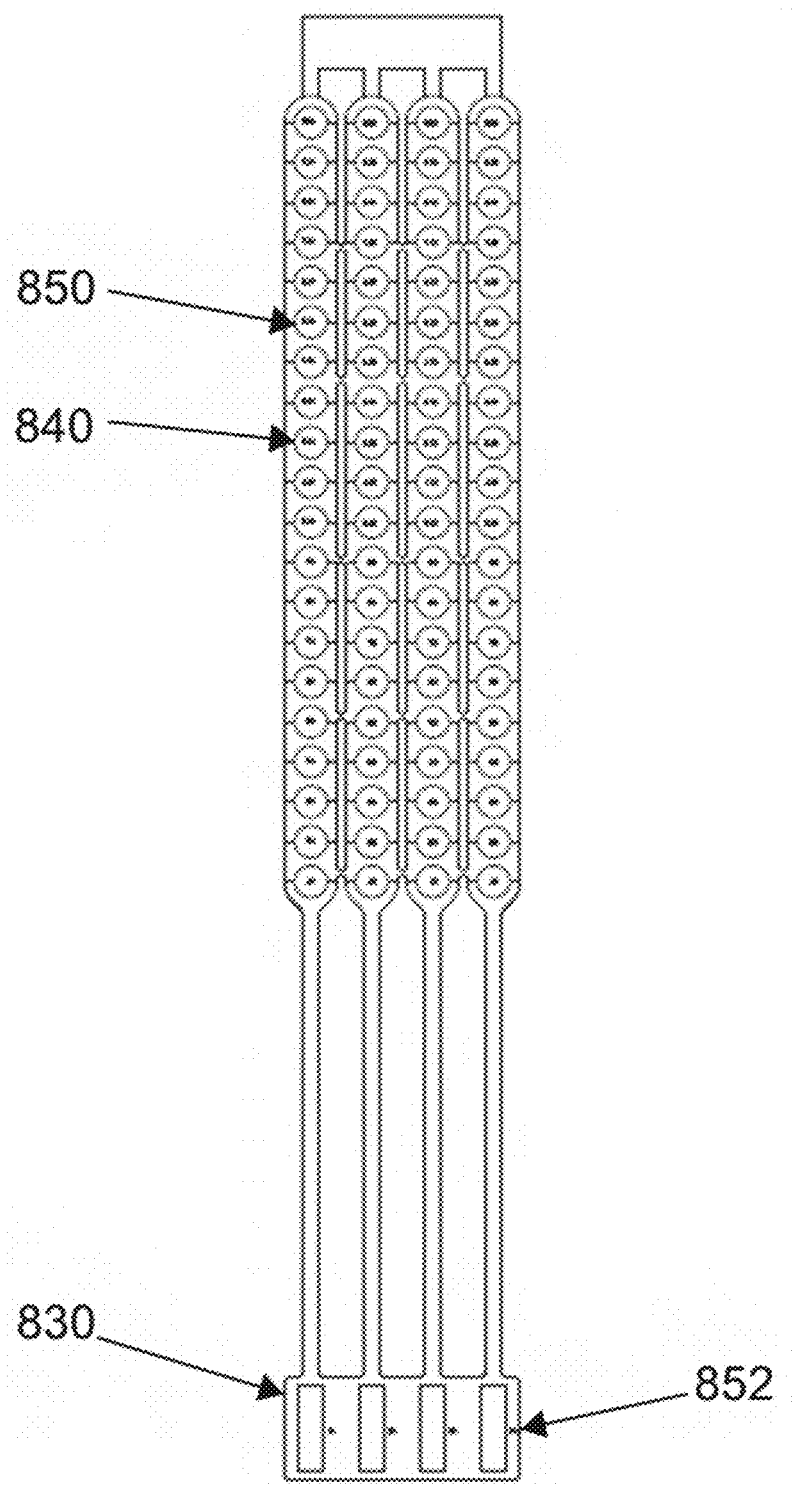
FIG. 10 is a diagram for a silkscreen layer used in fabricating one embodiment of the neural sleeve.

FIG. 10 is a diagram for a silkscreen layer 800 that can be used in fabricating the neuromuscular stimulation cuff device 110. The silkscreen layer 800 is applied to the combination of the conductive circuit layer 600 and coverlay layer 700 to identify individual electronic elements. A first silkscreen identification number 850 is provided to each electrode 840 so that it may be more easily found after visual inspection. In one embodiment, first silkscreen identification numbers 850 span from A1-A20 and D1-D20 to represent eighty individual electrodes 840. A second silkscreen identification number 852 identifies the connection ports for a rigidizer 830. In one embodiment, second silkscreen identification numbers 852 span from J1-J4. Both first and second silkscreen identification numbers 850, 852 are provided on a secondary side of the neuromuscular stimulation cuff 110, or side facing away from exposed electrodes 740. In an exemplary embodiment, silkscreen identification numbers 850, 852 are provided by white epoxy nonconductive ink.

Figure 11:
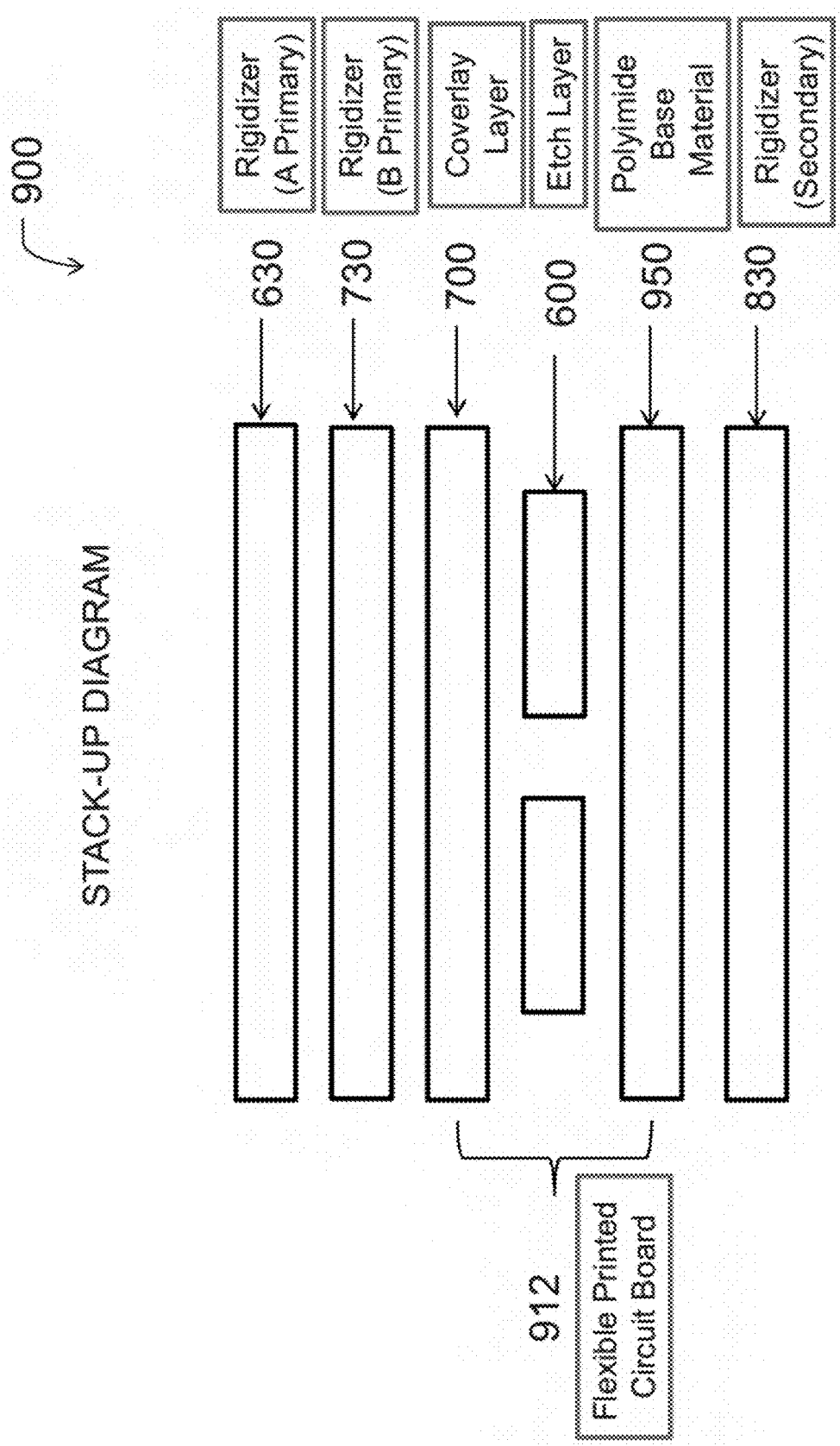
FIG. 11 is a stack-up diagram used in fabricating one embodiment of the neural sleeve.

Referring now to FIG. 11, various embodiments of the neuromuscular stimulation cuff device may be fabricated according to stack-up diagram 900. An insulating base material (e.g. polyimide) provides a substrate 950 upon which various components are fixed. A secondary side rigidizer 830 is laminated to a secondary surface of the substrate 950. The conductive circuit layer 600 is fabricated onto a primary surface of the substrate (opposite the secondary surface), and includes electrodes and traces that form conductive pathways on the flexible base substrate. The coverlay layer 700 is subsequently adhered to the conductive circuit layer 600 which covers the traces and leaves exposed portions of the electrodes. The combination of the substrate 950, conductive circuit layer 600, and coverlay layer 700 is defined as the flexible finger 912. Primary rigidizer 730 is stacked upon the coverlay layer to complete the electrical connection required to interface the flexible finger with the neural signal processor 104.

Figure 12:
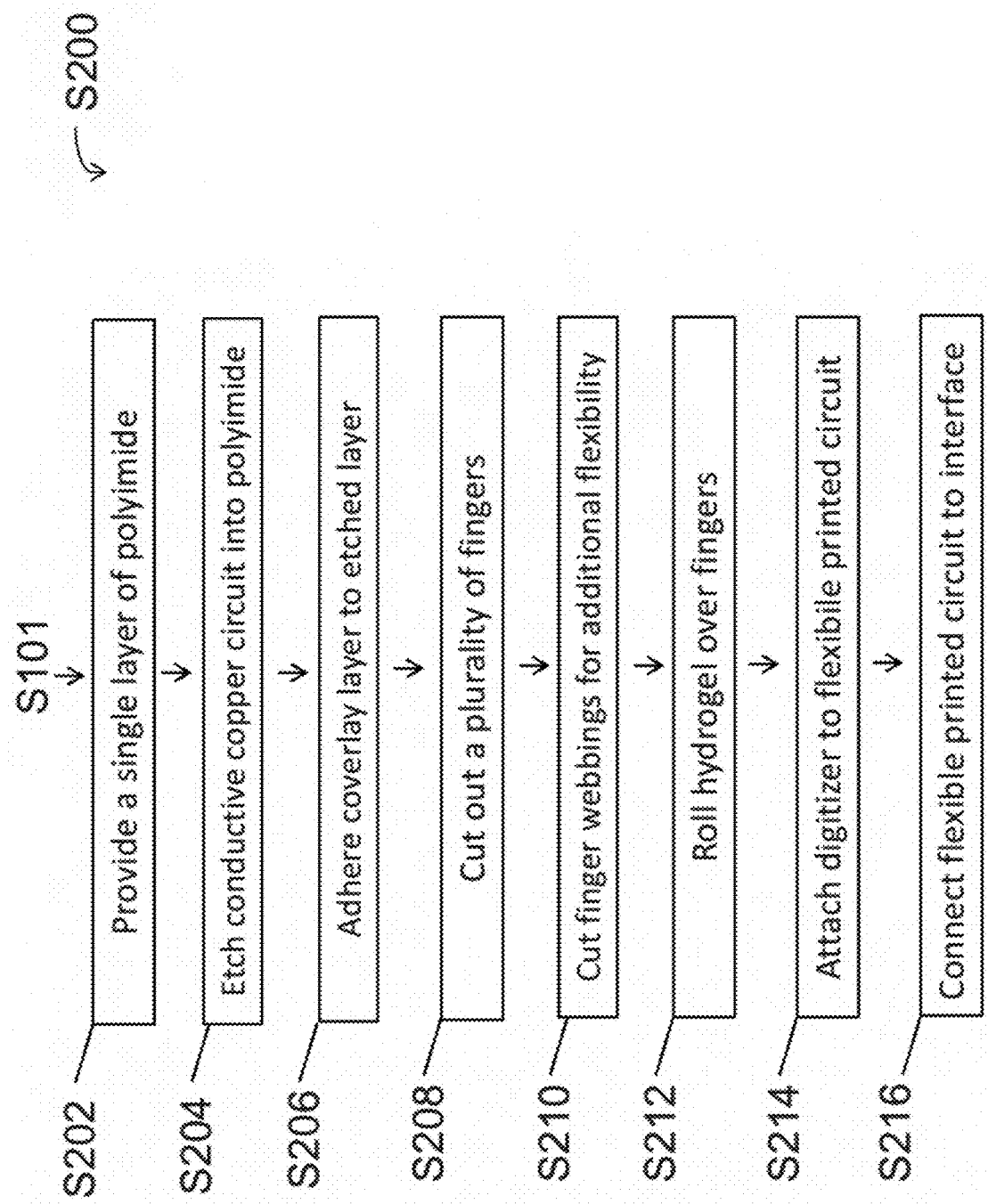
FIG. 12 is a flow diagram for one embodiment of a method for producing a neural sleeve.

With reference to the flow diagram set forth in FIG. 12, one embodiment of a method for producing a neuromuscular cuff S200 starts at S201. At S202 a single layer of polyimide base material 950 is provided. At S204, a conductive circuit layer is fabricated onto the polyimide base material 950 by etching a conductive copper circuit into the polyimide. At S206 a polyimide coverlay layer 700 is adhered to the conductive circuit layer 600. Adhering the coverlay layer 700 to the conductive circuit layer 600 completes the formation of a flexible PCB from which the flexible conductive pathways 912 will be formed. At S208, a plurality of flexible fingers are formed from the flexible PCB to provide additional contact points for stimulation of muscles or sensing EMG signals. At S210, finger webbings 725 may optionally be cut from the flexible PCB to separate the flexible fingers and provide additional flexibility, such as to accommodate limb twisting (such as the forearm) while maintaining contact. At S212, hydrogel may optionally be rolled over the electrodes to create electrogel discs 117. At S214, a rigidizer 630, 730, 830 is attached to the flexible fingers 912 for interfacing with the neural signal processor 104. At S216, the flexible fingers 912 are interfaced with the neural signal processor 104.

Figure 13:
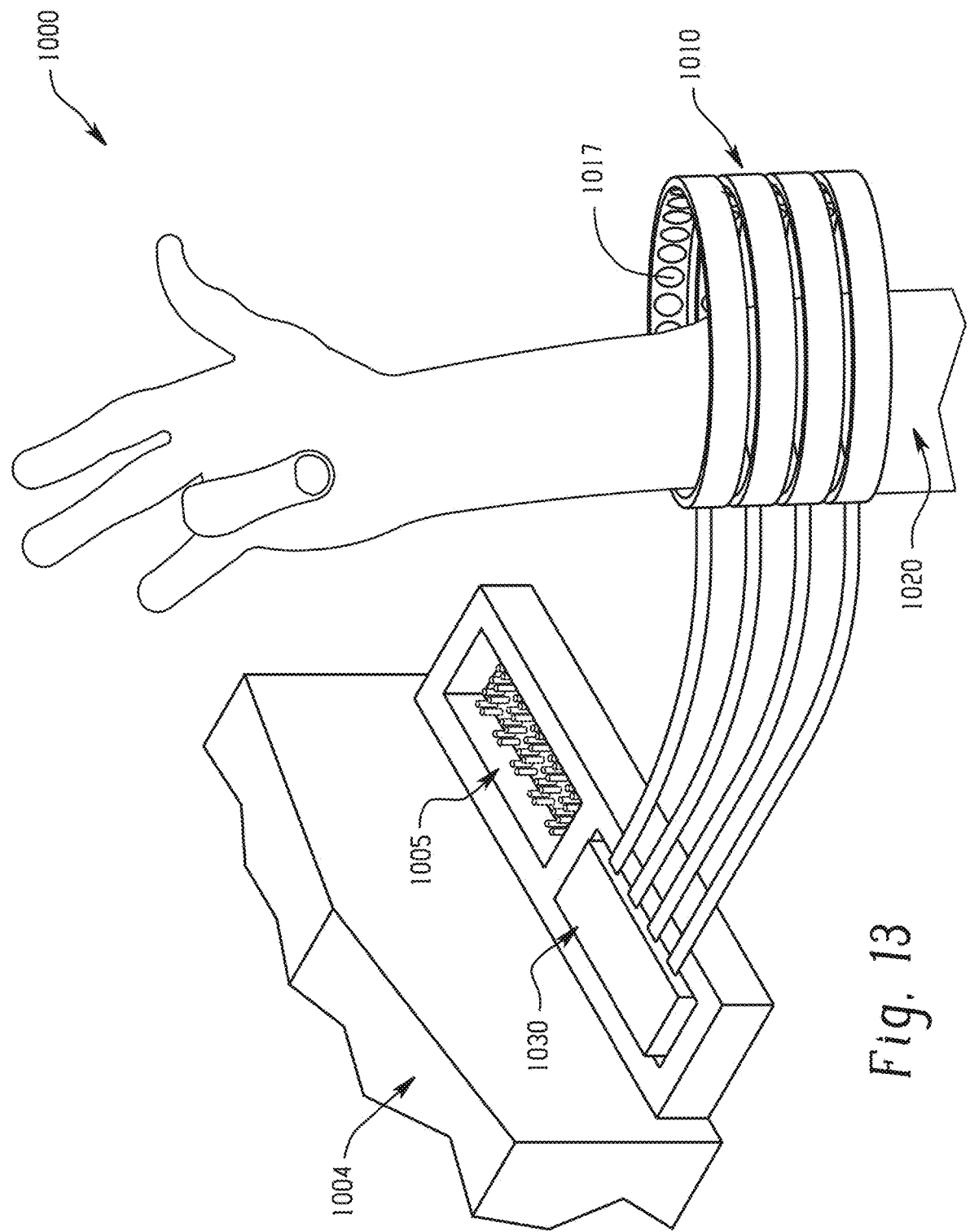
FIG. 13 is an exemplary photograph showing individual finger movement within a system for thought-controlled neuromuscular stimulation.

With reference to FIG. 13, individual finger movement within a system for thought-controlled neuromuscular stimulation 1000 is demonstrated. A neuromuscular cuff 1010 according to one embodiment is wrapped over a damaged or degenerative region 1020 of the nervous system. The neuromuscular cuff 1010 is interfaced with a neurological signal processor 1004 through attached rigidizer 1030. The rigidizer is attached to a connection port 1005 on the neural signal processor 1004. Received neurological signals indicative of patient thinking about moving their first two digits has been decoded and re-encoded into pulse train signals transmitted to various electrodes on the neuromuscular stimulation cuff 1010. Using a specific number and spacing of electrodes/electrogel discs 1017 in neuromuscular stimulation cuff 1010 has allowed for high resolution and non-invasive neuromuscular stimulation which effectuates the intention of the patient.

Electrogel discs 1017 operate in pairs when reanimating motion. Individual digit movement may be effectuated through the operation of two to three pairs (4 to 6 units) of electrogel discs 1017 which are stimulating in tandem. Selecting particular pairs of electrogel discs 1017 to reanimate motion as indicated by a decoded brain signal is advantageously performed by the neuromuscular stimulation cuff 1010, as each electrogel disc 1017 is connected to the neurological signal processor 1004 individually along a single traces etched into a conductive layer of flexible polyimide material.

Figure 14:
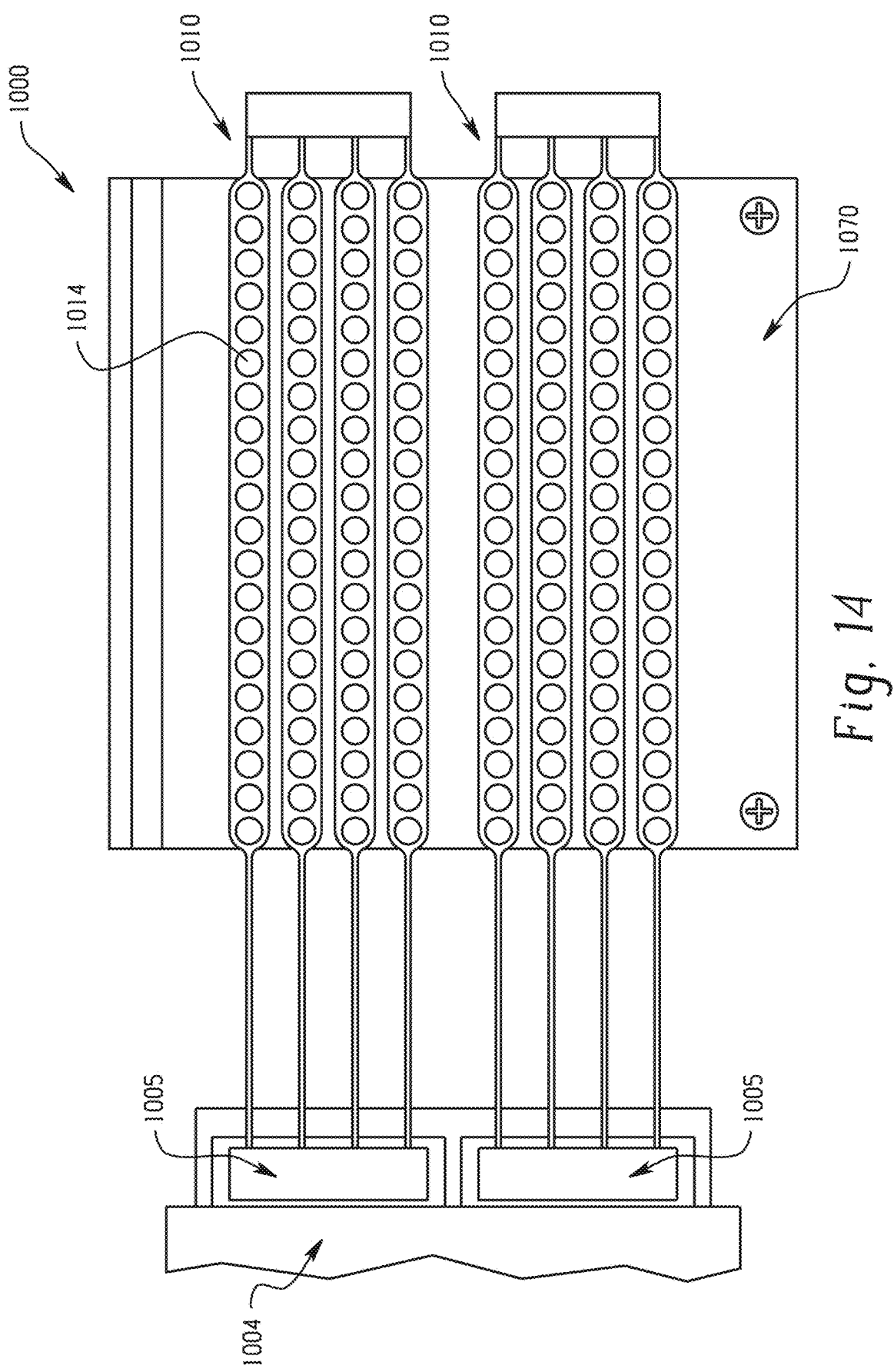
FIG. 14 is an exemplary photograph showing two neural sleeve devices according to one embodiment disposed on a preparation bench.

With reference to FIG. 14, two neuromuscular cuff devices 1010 according to one embodiment are disposed on a preparation bench 1070. The preparation bench 1070 may be used to keep cuff devices 1010 flat and roll hydrogel tape across electrodes 1016. Properly adhered hydrogel discs 116 (not shown) should fully cover the surface of electrodes 1014.

Figure 15:
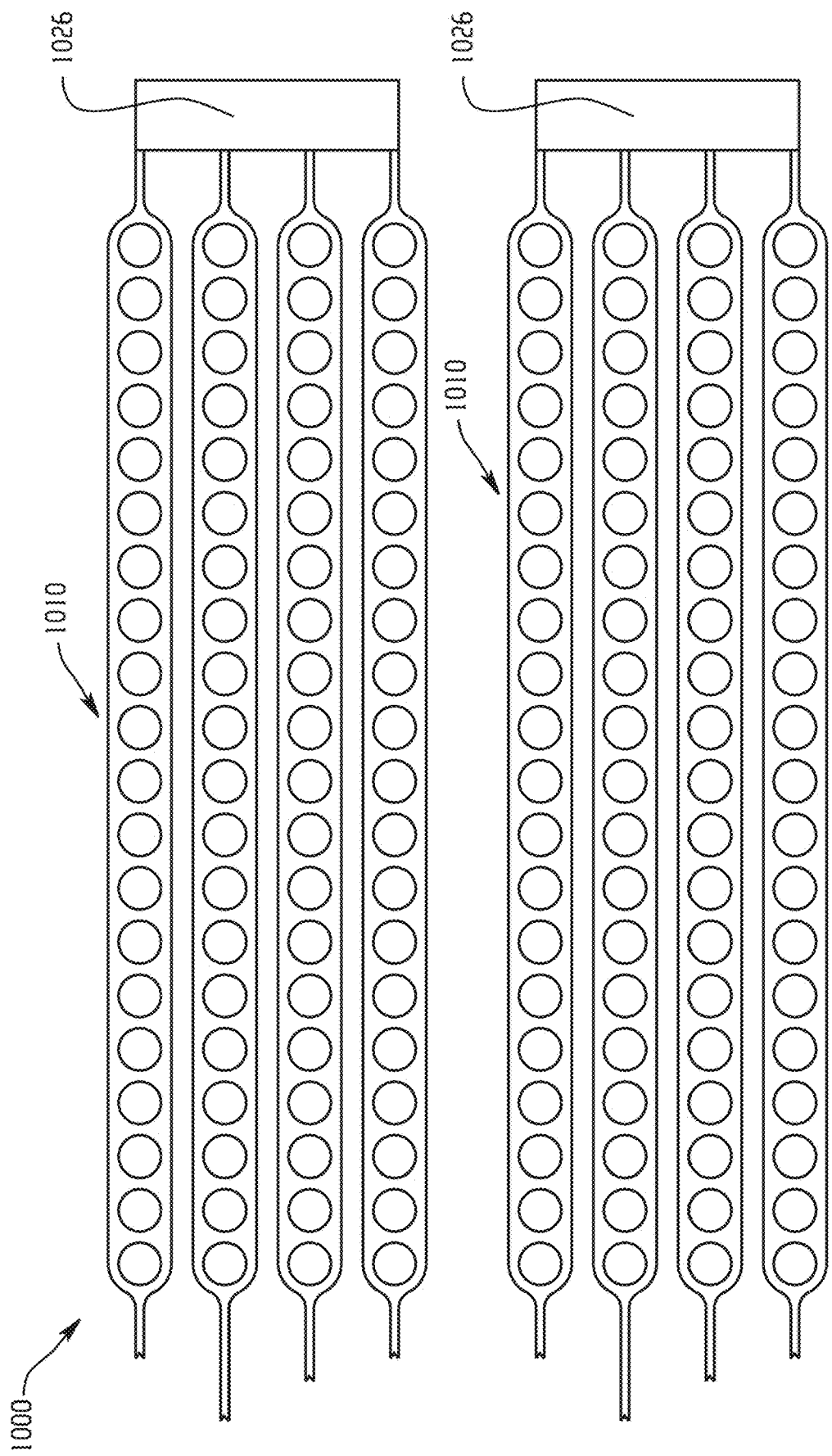
FIG. 15 is an exemplary photograph showing two neural sleeve devices according to the embodiment of FIG. 14.

With reference to FIG. 15, two neuromuscular cuff devices 1010 according to the embodiment of FIG. 14 are shown. The cuff devices 1010 each include a fork 1026 for additional support when designing and/or placing the cuff devices 1010 over a damaged or degenerative region/pathway of the nervous system (not shown). Again, the fork is optional.

Figure 16:
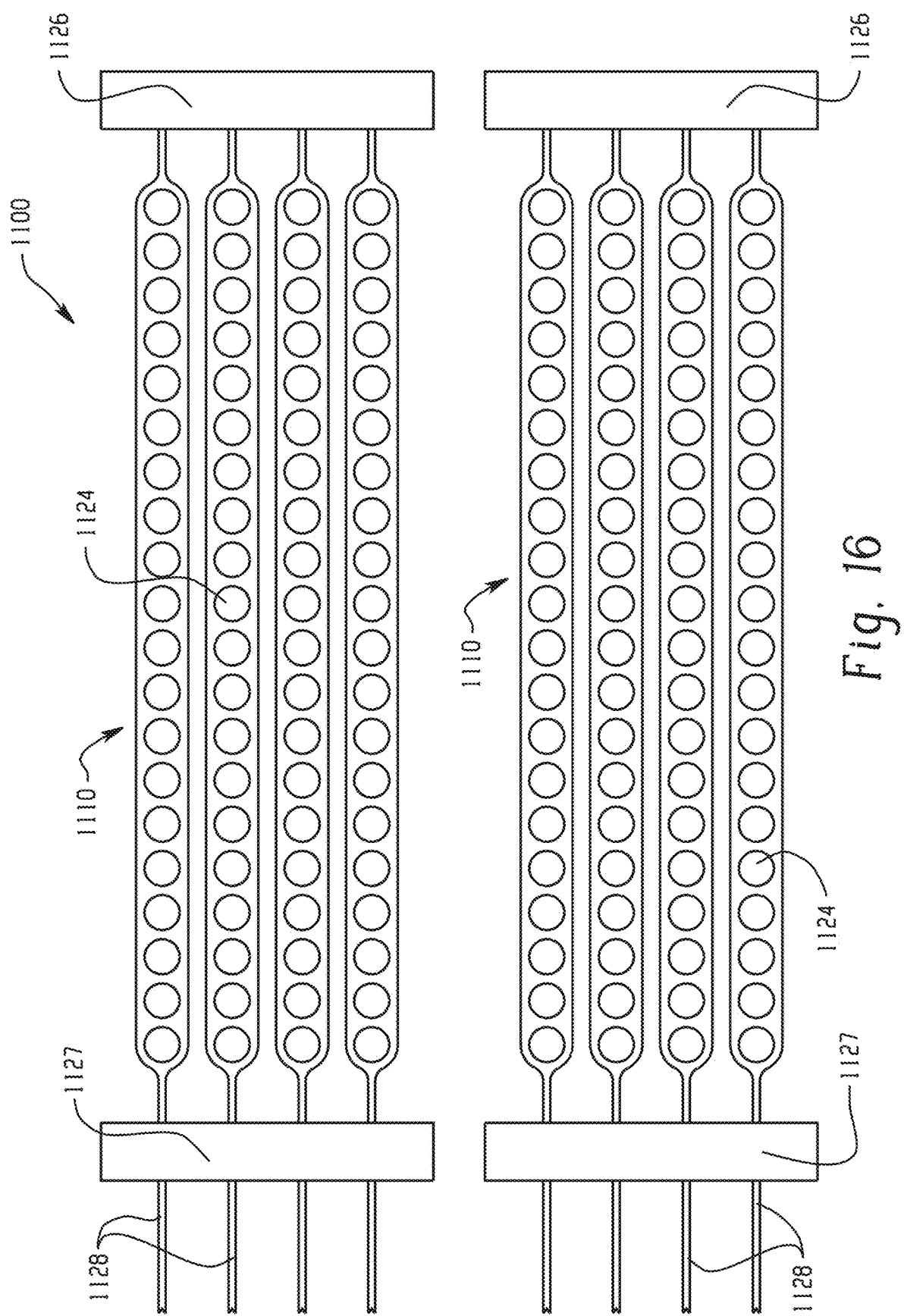
FIG. 16 is an exemplary photograph showing two neural sleeve devices according to a different embodiment.

With reference to FIG. 16, two neuromuscular cuff devices 1110 according to a different embodiment are shown. A fork 1126 is provided at one end of each cuff for additional design and/or structural support, similar to the fork 626 in FIG. 6. Here, a second fork 1127 is also provided located along the headers 1128. Put another way, the flexible fingers 1124 are bracketed by a fork on each end. The additional fork 1127 provides additional support in combination with fork 1126 for situations when the neuromuscular cuff 1110 must be stretched flat across a surface. Additional fork 1127 can also maintains flexible fingers 1124 within the same damaged or degenerative region/pathway 1120 (not shown), which effectively concentrates stimulation and prevents flexibility.

Figure 17:
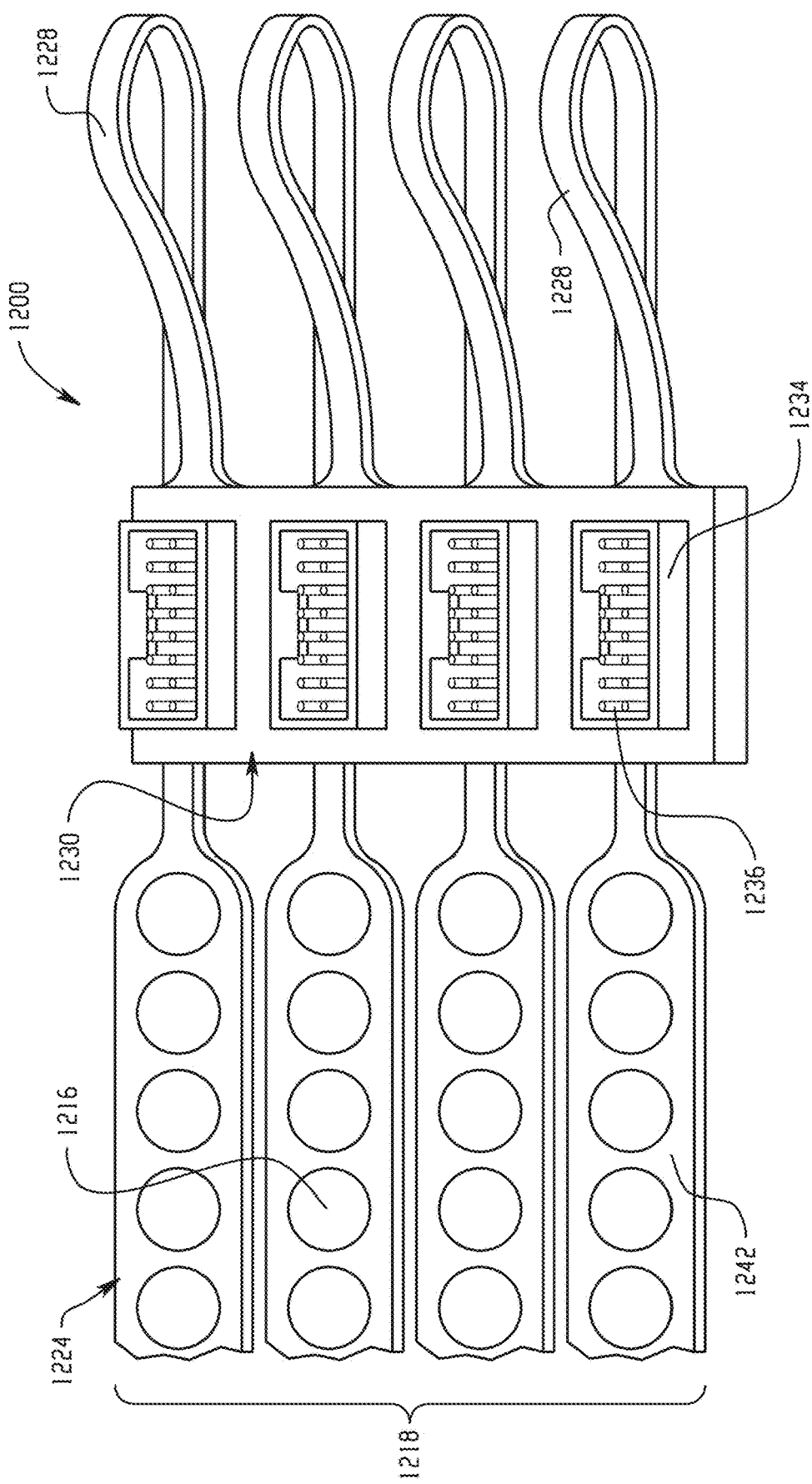
FIG. 17 is an exemplary photograph showing a rigidizer and the primary side of a neural sleeve device according to yet another embodiment.

With reference to FIG. 17, the primary side of another embodiment of the neuromuscular cuff 1200 is shown. Hydrogel discs 1216 have been applied to electrodes 1214 (not shown, covered), forming an electrogel disc array 1218. Two of the four flexible fingers 1224 still include the hydrogel tape before being separated from hydrogel discs 1216. Electrogel discs 1217 are not connected to each other within the array 1218 so that the electrogel discs 1217 may be independently stimulated.

While not exposed to the air, copper traces 1242 are viewable through the polyimide cover layer 700. A secondary side rigidizer 1230 is shown by folding the primary side over at the headers 1228. Connectors 1234 on the secondary side rigidizer 1230 allow for the neuromuscular stimulation cuff 1200 to be interfaced with the neural signal processor 104 (not shown). Each pin 1236 within connector 1234 is electrically connected with a single electrogel disc 1217.

Figure 18:
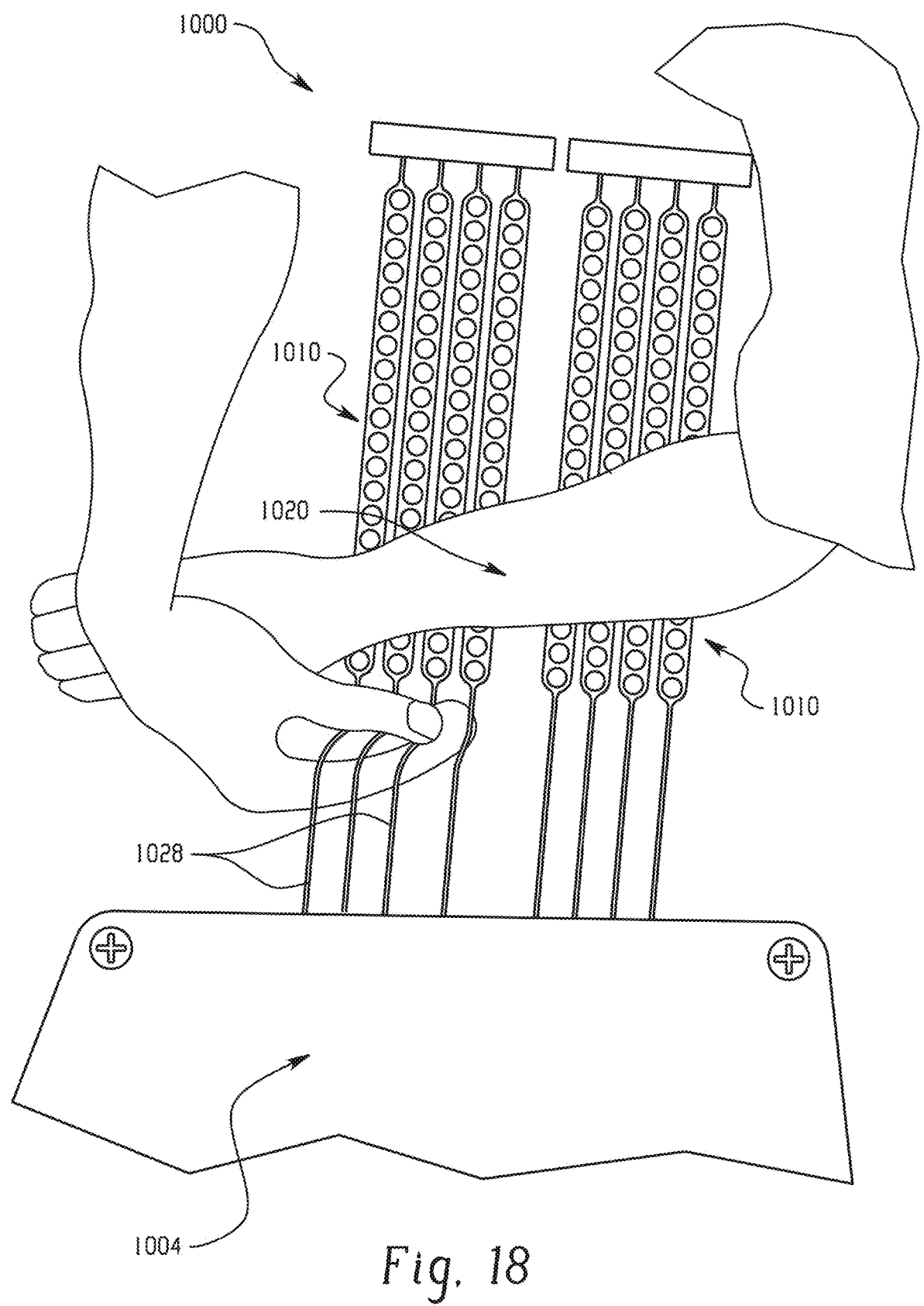
FIG. 18 is an exemplary photograph showing the positioning of a patient's arm region over two neural sleeve devices according to the embodiment of FIG. 14.

With reference to FIG. 18, a patient's arm including damaged or degenerative regions/pathways 1020 is placed over two neuromuscular cuff devices 1010 according to the embodiment of FIG. 14. Flexible headers 1028 may be used as support while positioning the device 1010 under an arm.

Figure 19:
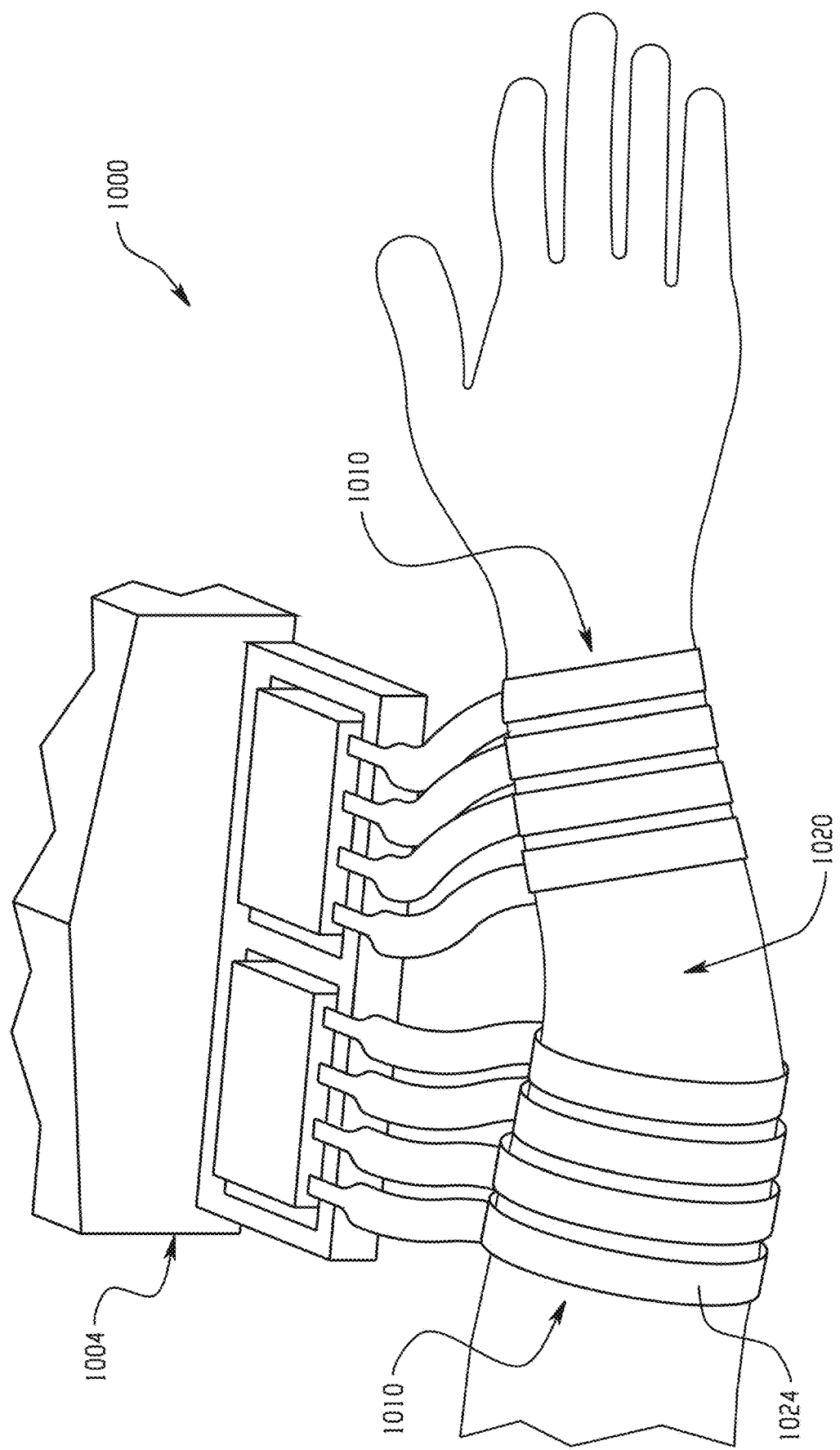
FIG. 19 is an exemplary photograph showing two neural sleeve devices according to the embodiment of FIG. 14 which are wrapped around a patient's arm region in preparation for neuromuscular stimulation.

With reference to FIG. 19, two neuromuscular cuff devices 1010 in an exemplary embodiment are wrapped around a patient's arm region 1020 in preparation for neuromuscular stimulation. The two cuff devices 1010 together provide 160 separate electrodes for stimulating finger or wrist movements. The flexible fingers 1024 permit the neuromuscular cuff to fit around the arm region 1020 at points of varying circumference. Hydrogel discs 1016 (not shown) keep both cuffs 1010 adhered to the arm.

Figure 20:
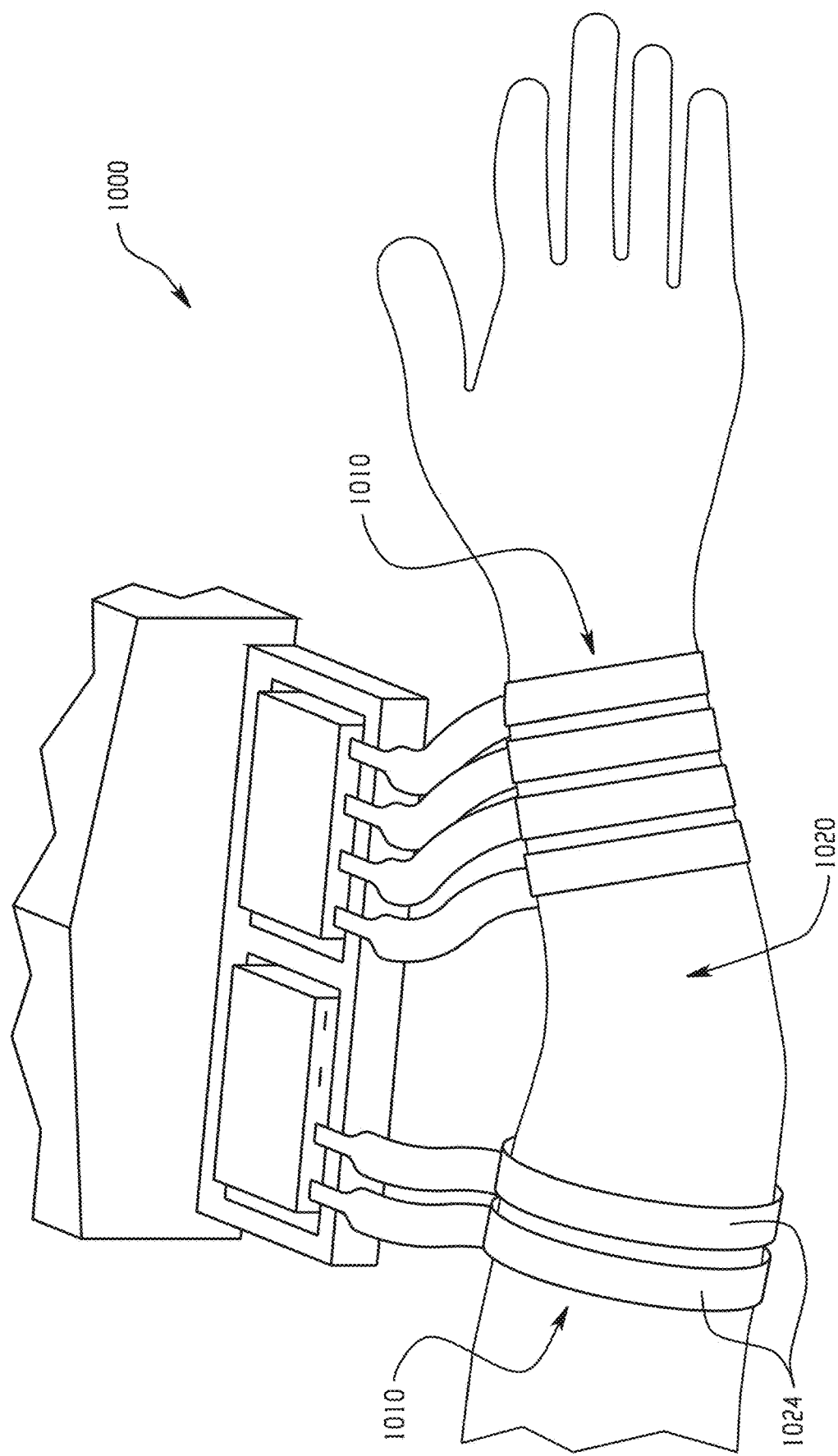
FIG. 20 is an exemplary photograph showing two neural sleeve devices according to the embodiment of FIG. 14 which are alternatively wrapped around a patient's arm region in preparation for neuromuscular stimulation.

With reference to FIG. 20, two neuromuscular cuff devices 1010 according to the embodiment of FIG. 14 are alternatively wrapped around a patient's arm region in preparation for neuromuscular stimulation. Only two flexible fingers 1024 of one of the neuromuscular cuff devices 1010 have been applied, while all of the flexible fingers 1024 on the other cuff device 1010 are already wrapped around the patient's arm. More or less electrodes can be used, as shown in FIG. 20, depending on the nature of the damage to a patent's nervous system region/pathway 1020 and the type of movement one wishes to reanimate through neuromuscular stimulation.

Figure 21:
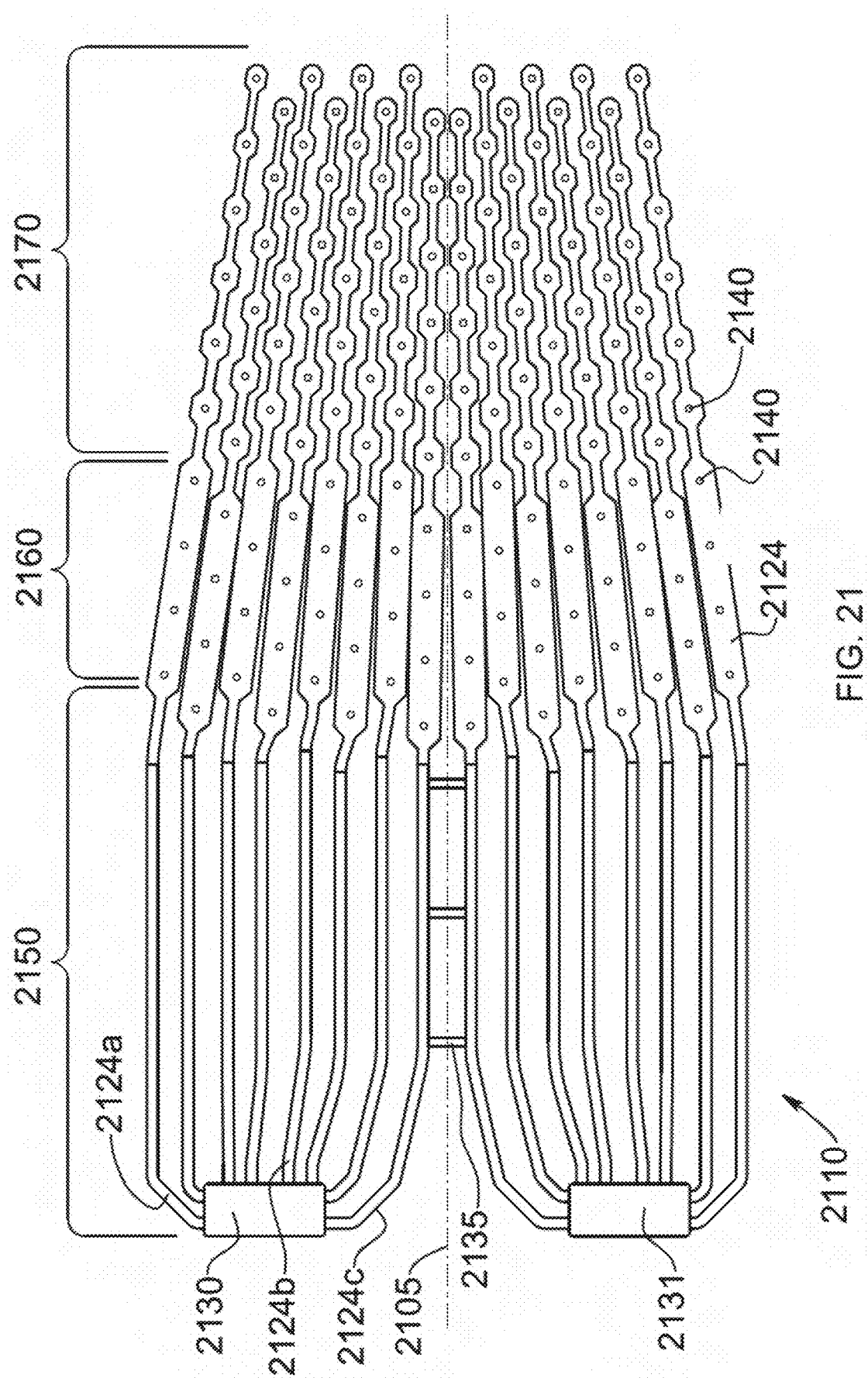
FIG. 21 is diagram of another exemplary embodiment of a neural sleeve. In this embodiment, conductive pathways extend from two different connectors. The fingers extend in the same direction, and taper towards a center axis.

In another exemplary embodiment, the flexible fingers of a neural sleeve 2110 do not need to be straight for their entire length. Referring now to FIG. 21, flexible fingers 2124 extend from first connector 2130, which has a rectangular shape in this illustration. The flexible conductive pathways 2124 in this embodiment "change" directions as they extend from connector 2130. For example, an upper flexible finger 2124*a* first extends upwards from the connector 2130, then changes direction so that its electrodes 2140 are to the right of the connector 2130. A center flexible finger 2124*b* extends from the right-hand side of the connector 2130 off to the right of the connector. A lower flexible finger 2124*c* first extends downwards from the connector 2130, then changes direction so that its electrodes 2140 are also to the right of the connector 2130. Notably, none of the electrodes 2140 are present to the left of the connector 2130.

This embodiment of a neural sleeve 2110 also contains more than one connector/rigidizer. As illustrated here, the neural sleeve 2110 has a first connector 2130 and a second connector 2131. Flexible fingers extend in the same direction (here, to the right) of both connectors. Webbings 2135 connect flexible fingers extending from each connector 2130, 2131. There may be any number of webbings 2135, and the webbings 2135 may connect the flexible fingers at any portion of their length. Here, the webbings 2135 are present along a non-electrode-containing portion 2150 of the flexible fingers (i.e. the header portion). Though not depicted, it is specifically contemplated that the flexible fingers of one connector 2130 may be of a different length from the flexible fingers of the other connector 2131.

The electrodes 2140 may be evenly spaced apart along the length of the flexible fingers 2124, or their spacing may vary, for example becoming shorter or longer, as the distance from the connector 2130 increases. For example, muscle segments get smaller closer to the wrist, so the electrodes need to be closer together as well. However, the electrodes do not need to be present along the entire length of the flexible fingers. As seen here, the flexible fingers 2124 may include a non-electrode-containing portion 2150 extending from the connector, which is similar to the header 528 of the embodiment of FIG. 5. The flexible finger may also include a non-scalloped electrode-containing portion 2160, and a scalloped electrode-containing portion 2170 at the distal end of the flexible finger (i.e. distal from the connector). It should be noted that none of the flexible fingers overlap with each other.

The electrode-containing portions 2160, 2170 of the flexible fingers have a different shape from each other. One reason for this difference in shape is because, as seen here, the distal ends of the flexible fingers 2124 extend inwardly towards a center axis 2105 of the neural sleeve 2110. Put another way, the flexible fingers 2124 taper inwards towards the center axis 2105. The scalloped portions 2170 of adjacent flexible fingers permit them to fit into a smaller area while still providing a suitable number of electrodes (note the electrodes do not change in size). However, the flexible fingers 2124 all still extend in the same direction away from the connector 2130, i.e. to the right in this figure. Put another way, the flexible fingers comprise a first portion which is transverse to the center axis 2105, and a second portion which is parallel to the center axis. These portions are particularly seen in the flexible finger 2124*a*, which first extends upwards (i.e. transversely to the center axis), then extends parallel to the center axis.

This particular embodiment is intended to be used on a patient's arm with the two connectors 2130, 2131 located near the shoulder, and the scalloped portions 2170 near the wrist and hand.

In other exemplary embodiments, it is contemplated that the neural sleeve will include both an outer, reusable component, and an inner, disposable component. Advantageously, this allows for a reduced per-use cost for the outer component, while permitting multiple different persons to use the outer component without hygienic concerns. The outer reusable sleeve contains the electrodes.

It is contemplated that the outer sleeve/reusable component, in several embodiments, could be made of a flexible, stretchy, and/or compressible fabric material which would fit snugly against the user's arm. The material could also be a dry-fit material, i.e. a material which can move sweat away from the user's arm and permit the sweat to evaporate. The connector and flexible fingers would line the interior of the outer sleeve. For example, conductive threads or fibers could be woven into the fabric material. Alternatively, the conductive traces and electrodes could be printed onto the outer sleeve material using silk-screen technology, for example using conductive polycellulose, a silver-based ink, or carbon-based ink.

Figure 23:
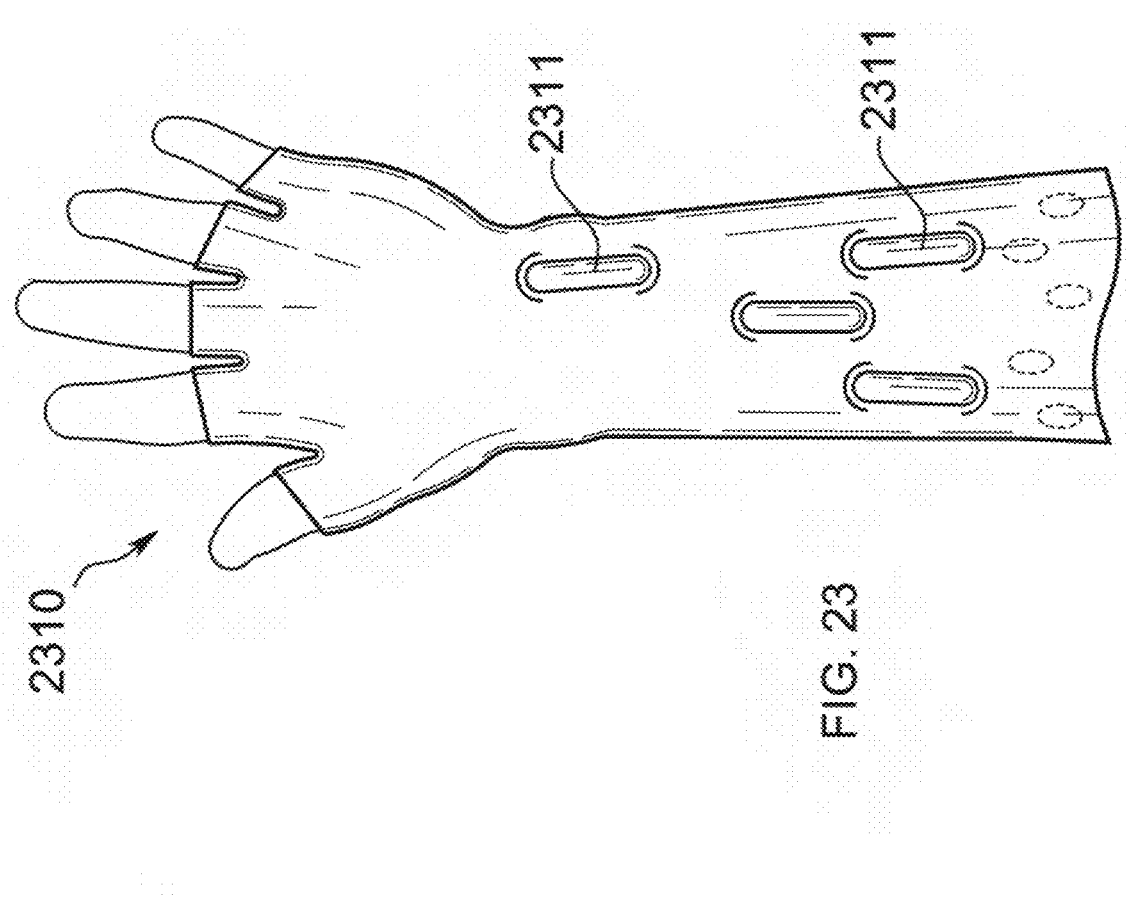
FIG. 23 is an exemplary illustration of a variation of the neural sleeve of FIG. 22, in which the neural sleeve includes a user interface on the exterior in the form of buttons.
Figure 22:
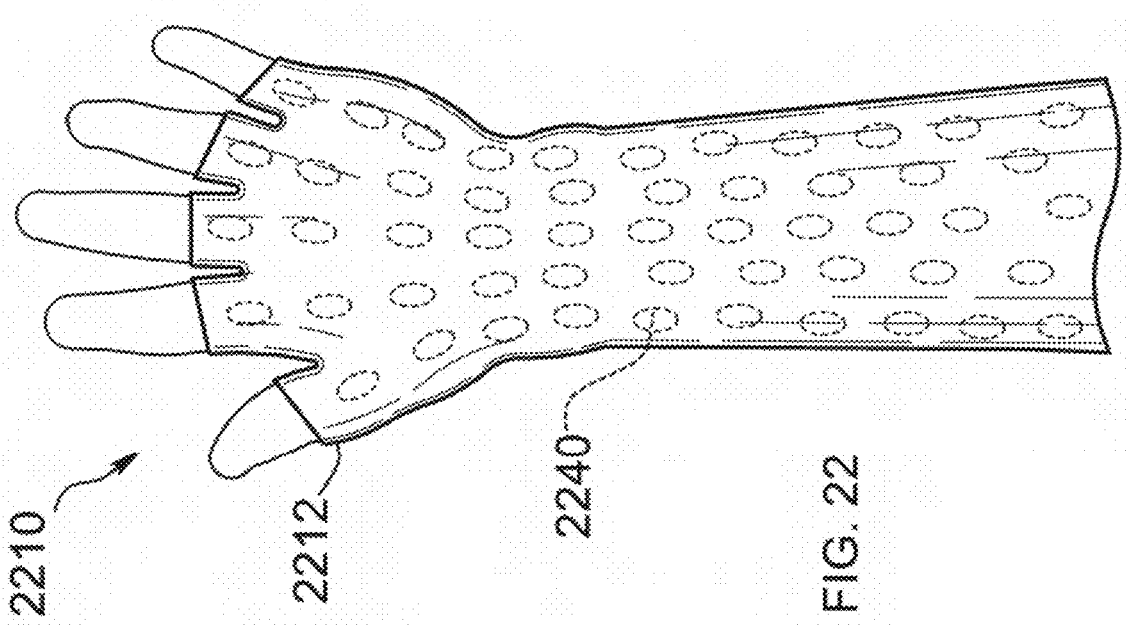
FIG. 22 is an exemplary illustration of a fingerless neural sleeve in the form of a glove that can reach up to the elbow.

FIG. 22 and FIG. 23 show one exemplary embodiment of this neural sleeve. FIG. 22 is an illustration of a neural sleeve 2210 which is in the form of a fingerless glove. Not visible in FIG. 22 is an inner sleeve containing a conductive medium. FIG. 23 is an illustration of a variation on the neuosleeve outer component. As illustrated here, the neural sleeve 2310 has a user interface on the exterior reusable component, which can be used for control (including registration, activation, configuration and so forth) of individual electrodes or groups of electrodes, allowing a user to configure the electrodes or adjust a stimulation level or pattern. For example, the outer component may include buttons 2311 (e.g. in the form of LED-based touchscreens). While only four buttons are illustrated here, the user interface can include any number of buttons, and those buttons can be of any shape.

Figure 24:
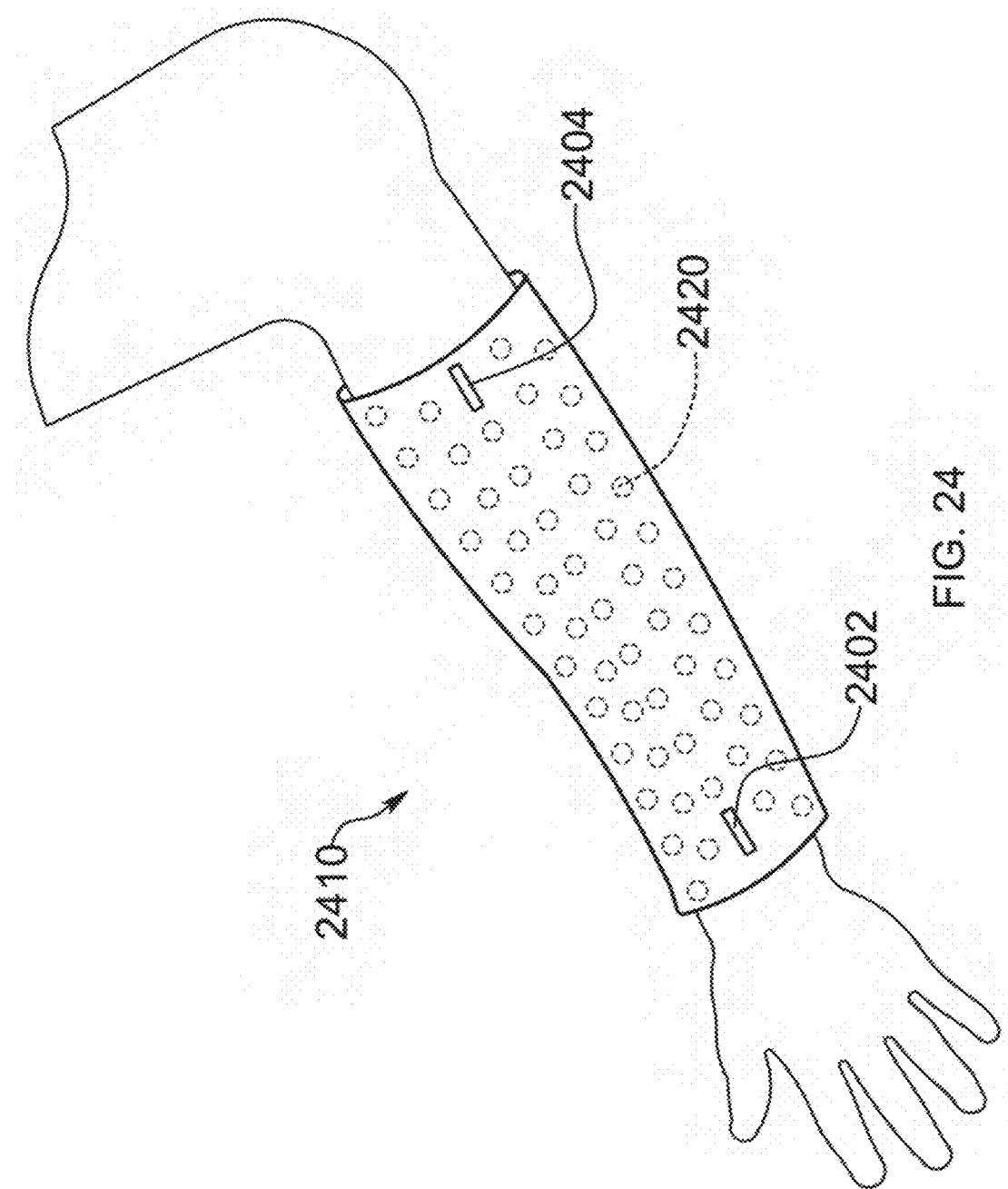
FIG. 24 is an exemplary illustration of a neural sleeve made of a flexible material with electrodes on the interior and implants for providing directionality to the neural sleeve.

Another aspect of the present disclosure is illustrated in FIG. 24. The neural sleeve itself may be made in a bidirectional manner, i.e. both ends of the sleeve are of the same construction. It is contemplated that directional implants 2402, 2404 could be used to provide directional information to the neural sleeve 2410, e.g. which end of the neural sleeve is closer to the elbow or the wrist. These implants may be located in the patient's limb, or located at opposite ends of the neural sleeve itself. Only one such implant is needed to identify the orientation/direction of the neural sleeve. It is noted that three-dimensional information can also be provided by such implants. Also depicted are the electrodes 2420.

Figure 25:
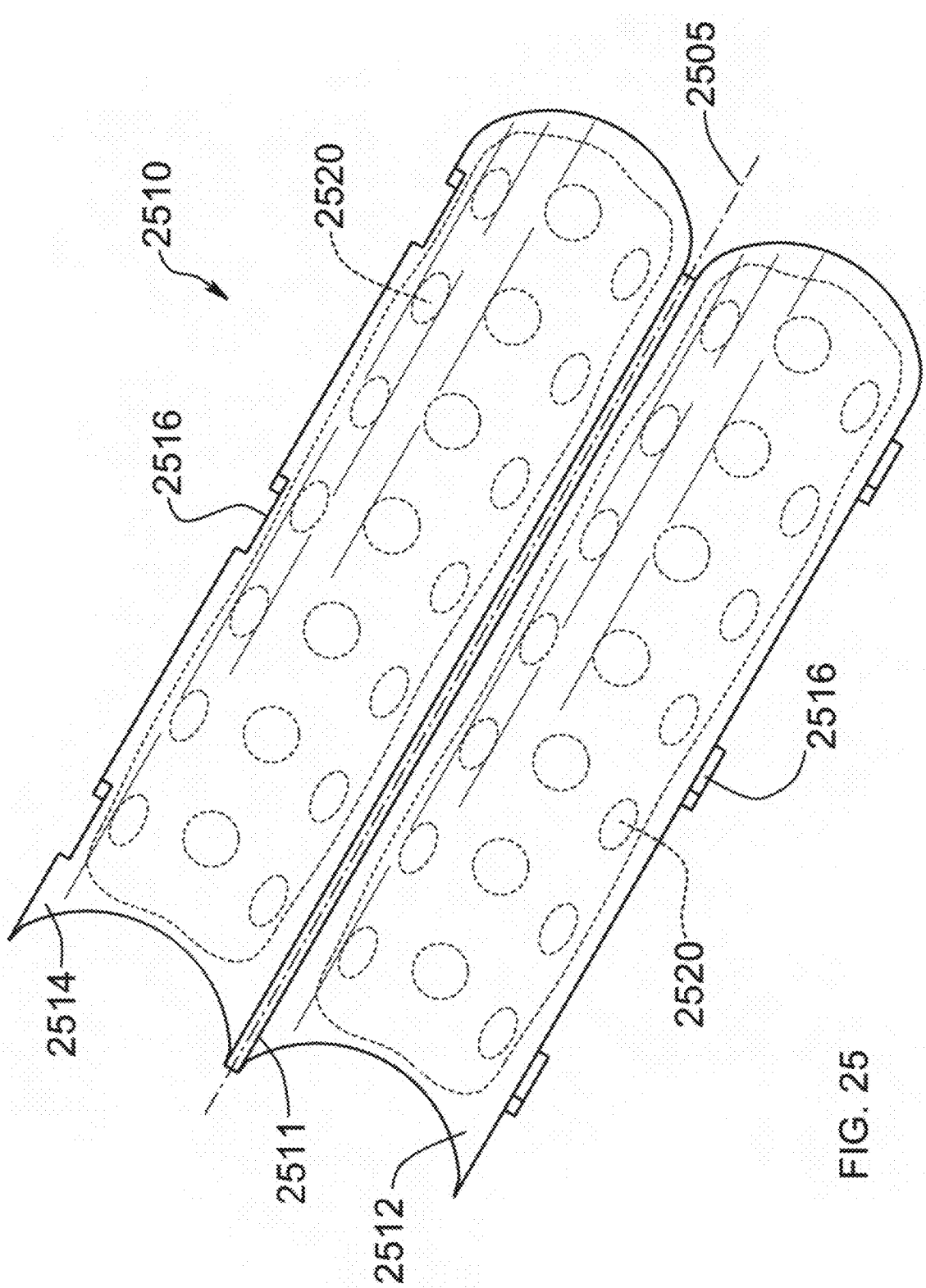
FIG. 25 is an exemplary illustration of a neural sleeve in the form of a rigid shell having two hemicylindrical halves joined together by a hinge along the sidewall.

FIG. 25 is another embodiment of the reusable outer component. Here, the outer component is in the form of a rigid shell 2510. The shell is separated into two hemicylindrical halves 2512, 2514 which are joined together by a hinge 2511. The hinge runs parallel to the longitudinal axis 2505 of the shell. A closing mechanism 2516 is located on opposite open ends of the halves for keeping the shell closed once it is closed around the user's limb. Within the shell is padding for conforming the shell to the user's limb, or a bladder that can be inflated with air. The shell houses the electrodes 2520 (which are used for both sensing and delivering neuromuscular stimulation), as well as other accompanying electronics. It is contemplated that the disposable inner component (not shown) is first applied to the inside of the shell, or reusable dry electrodes are attached to the inside of the shell. Then the limb is placed in the shell, the shell closes around the limb, and the soft padding conforms around the limb and applies pressure on the electrodes against the limb, or the air bladder is inflated to apply pressure to the electrodes against the limb.

Figure 26:
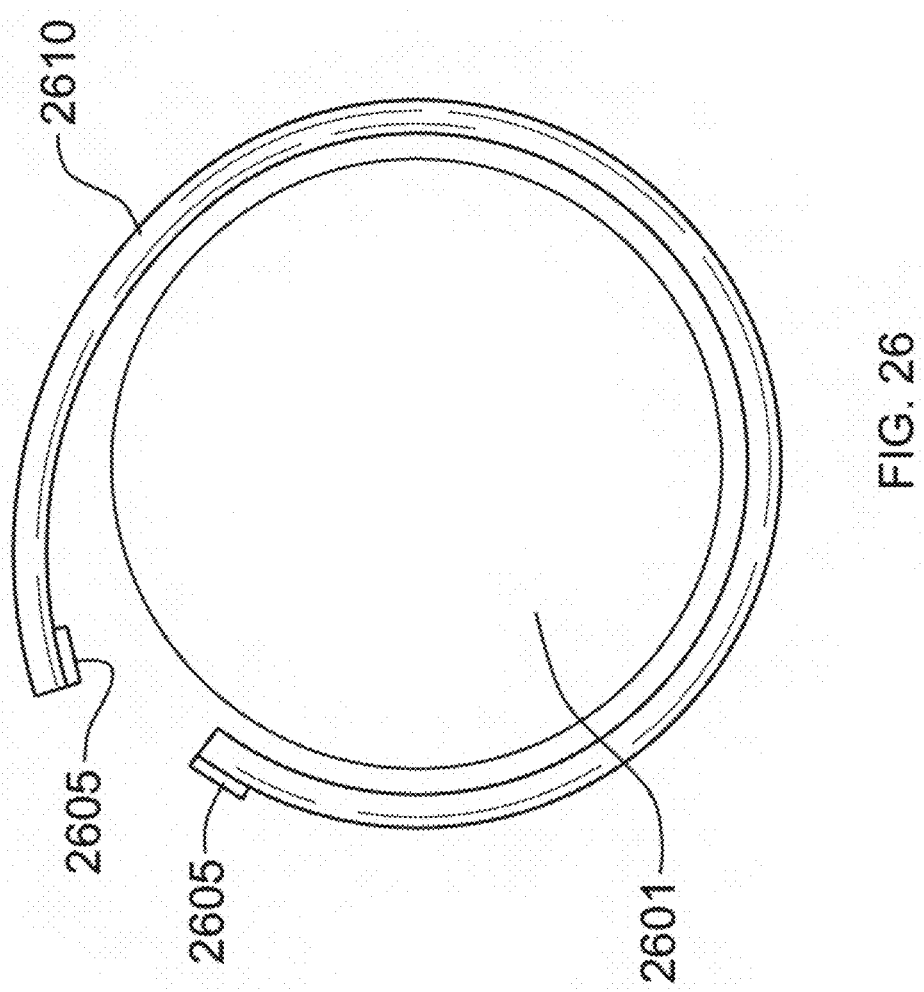
FIG. 26 is a cross-sectional illustration of a reusable neural sleeve, which is in the form of a flat flexible sheet that can be wrapped around the arm.

Alternatively, as seen in the cross-sectional view of FIG. 26, the neural sleeve can be in the form of a flexible sheet 2610 which is wrapped around the user's limb 2601. The electrodes (not visible) are spaced throughout the flexible sheet, and a closing mechanism 2605 is present on opposite ends of the sheet. Such a mechanism may be, for example, a hook-and-loop fastener.

Figure 27:
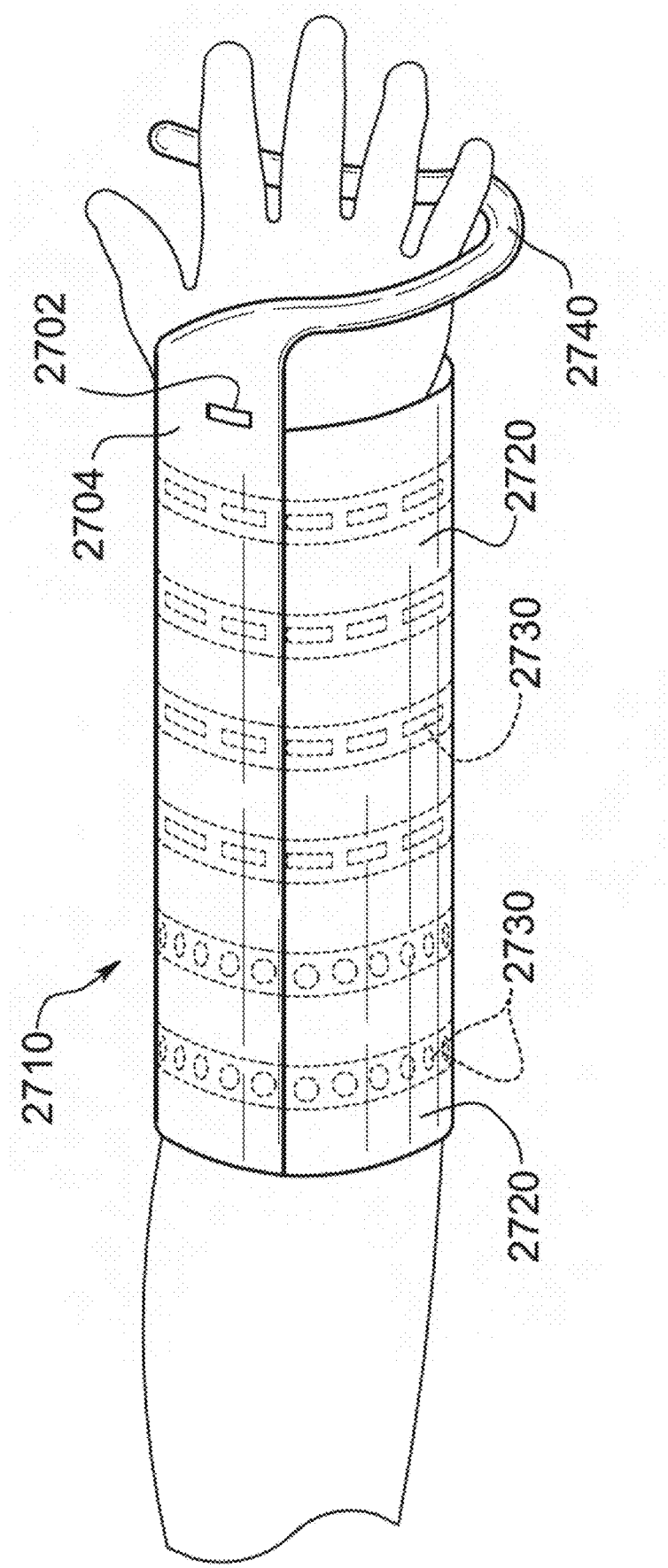
FIG. 27 is an exemplary illustration of a neural sleeve with expandable bladders for pushing the electrodes against the skin. A handle can be included with the sleeve for proper registration/orientation of the neural sleeve.

FIG. 27 illustrates another potential embodiment of the neural sleeve.

Desirably, the electrodes are fitted snugly against the patient's limb. In this embodiment, the neural sleeve 2710 contains bladders 2720 that can be filled with air or some fluid, causing the neural sleeve to expand and push the electrodes 2730 against the limb. A pneumatic pump can be used to fill the bladders. A directional implant 2702 is also present here at a distal end 2704 of the sleeve. In addition, a handle 2740 is also present at the distal end of the sleeve. This handle is intended to help with registration of the electrodes in known positions, and also provides directionality to the neural sleeve.

The neural sleeve can incorporate several different types of sensors to provide information on data and feedback on the position and movements of the limb and other body parts. For example, desired position information from the sensors can include a 3-dimensional location (X, Y, Z coordinates) of various points on the hand and arm relative to the body and to each other, and rotation information of the wrist, elbow, and shoulder relative to the body. Orientation of various body parts with respect to gravity can also be measured with an accelerometer (or inclinometer). Motions of the hand and arm may be derived from position sensors or from independent sensors. Other desired information includes joint angles at the elbow, wrist, thumb and fingers (or other body joints). A variety of concepts for sensors may be used to measure one or more of these data items. Broad categories of sensors include accelerometers, micro-electromechanical (MEMS), electronic (based on resistance, capacitance, or resonance), fluid bladders, optical fiber bend sensors, and video tracking systems. Again, these concepts can be generally applied to a neural sleeve on any body part or limb (e.g. arm, hand, leg, foot, etc.).

Figure 28:
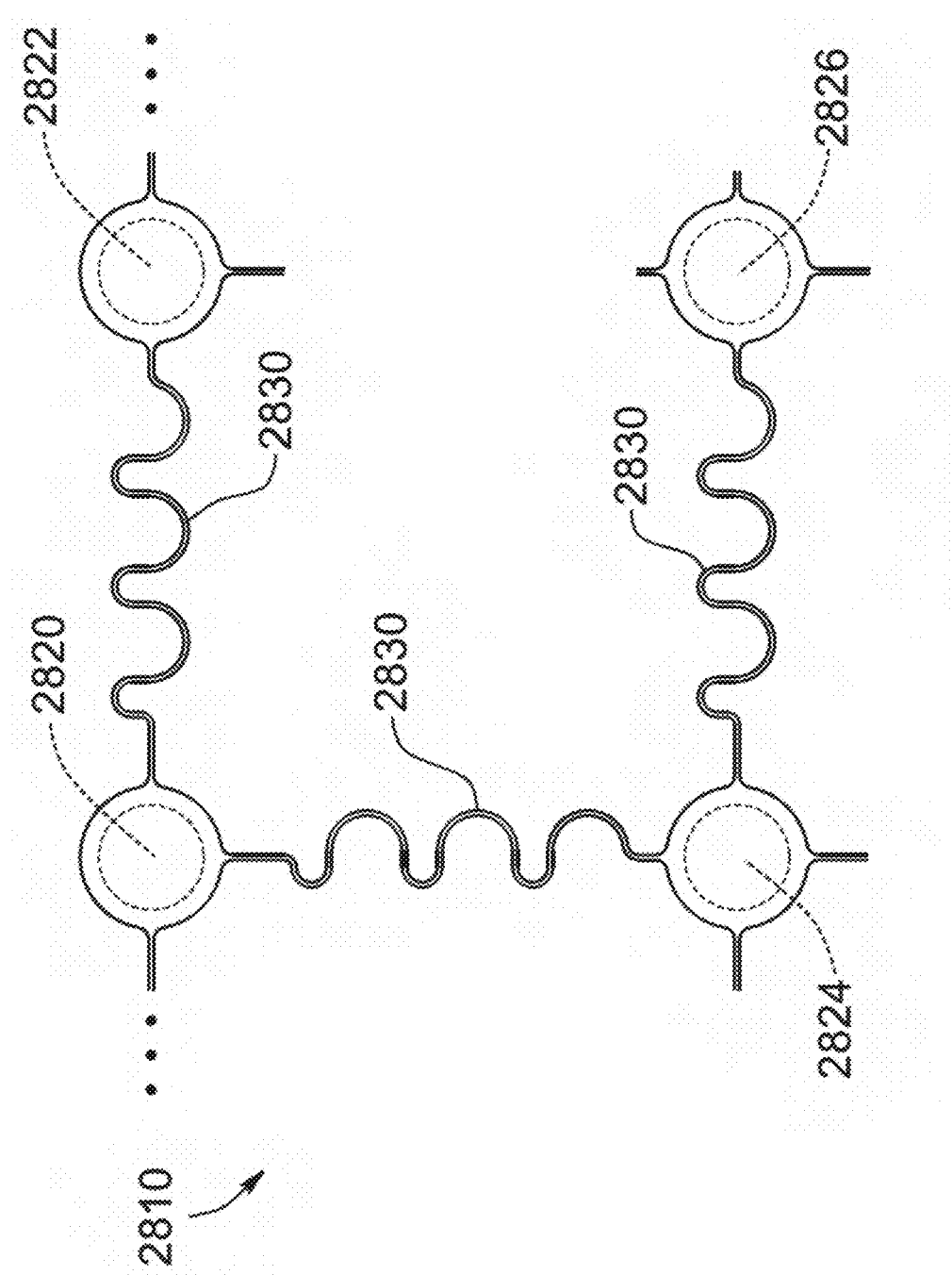
FIG. 28 is an exemplary magnified illustration of the construction of the flexible conductive pathways of the neural sleeve. These pathways can include electrodes as well as other components, for example strain gauges.

FIG. 28 illustrates some aspects which can be used for sensing. This is a magnified picture of a flexible conductive pathway 2810. Electrodes 2820 are present on the flexible conductive pathway. Here, four electrodes 2820, 2822, 2824, 2826 are illustrated. Electrode traces 2830 are present between the electrodes. As seen here, the trace have a zig-zag pattern, which can be used as a strain gauge.

In a first sensor aspect, integrated 6-axis MEMS (3-axis accelerometer and 3-axis magnetometer) sensors can be used to measure the position and orientation of the elbow and wrist relative to the location of the shoulder (e.g. the top of the humerus bone). When combined, these sensors can provide a reference frame utilizing the Earth's local gravitational (center of Earth) and magnetic (magnetic north) fields. Using this reference frame in conjunction with a defined 3-axis Cartesian coordinate system, different joints can be located in both position (X, Y, Z) and orientation (w (yaw), e (pitch), q (roll)) relative to the origin of the Cartesian coordinate system at the shoulder using these same MEMS sensors. Adjacent MEMS sensors can be placed at strategic locations where the length between sensors does not change (or the change is a sufficiently small amount) when the joints are bent or rotated. For example, sensors can be placed at locations on the shoulder, elbow, and wrist where the distance between adjacent sensors remains fixed due to fixed bone lengths.

The calculation of position and orientation of each joint may use the 3-axis Cartesian coordinate system and reference frame, the fixed distance between adjacent sensors, and the 3-axis output signals from the accelerometers or magnetometers. Calculations may involve direction cosine matrices, Euler transformations, or matrix multiplication. For sensors that are not adjacent to the origin, their coordinates may be transformed back to the coordinate system origin through intermediate transformations between adjacent sensors. For example, if there are sensors at the shoulder, elbow, and wrist then the elbow coordinates can be calculated directly relative to the origin (shoulder), but the wrist coordinates must first be calculated relative to the elbow coordinates and then calculated again relative to the origin. The reason for this is because the path lengths must be known for each sensor location and the only way to do this is by coordinate transformations along fixed length paths (e.g., wrist to elbow and elbow to shoulder).

A wide range of MEMS sensors with integrated 3-axis accelerometers and magnetometers may be used. Examples of manufacturers of these devices include Analog Devices, Bosch, Freescale, Honeywell, and ST Microelectronics. Also, 9-axis sensors available with integrated 3-axis, accelerometers, magnetomers, and gyros may be used. Additional solutions may exist for joint locations where a fixed bone length cannot be counted on such as the hand and fingers.

In a second sensor aspect, a capacitive sensor may comprise a flexible insulating dielectric layer with thin flexible electrodes on either side. A voltage differential is applied between the electrodes, creating a capacitor. When the dielectric changes shape (e.g. due to pressure or bending), the capacitance of the sensor changes and can be detected by electronic measuring techniques. Capacitive pressure sensors may be used in a variety of mechanical systems to measure barometric pressure or pressures inside equipment. Such sensors may be incorporated into the sleeve at joints (e.g. wrist, elbow) such that bending of the joint stretches or bends the dielectric layer. The sensors may also be applied away from joints (e.g. middle of the forearm) to measure the pressure of the sleeve against the arm.

In a third sensor aspect, resistive bend or stretch sensors (e.g. strain gauges) may be used. These sensors may be made from any material that changes electrical resistance when stretched or strained. This change in resistance is measured with a standard electrical circuit. Strain gauges may use metal, either alone or applied to a flexible thin film substrate. Resistive bend sensors or strain gauges also can be made from the following three general classes of materials. First, elastomers (such as silicone rubber) or polymers containing electrically conductive fillers may be used. Fillers can include carbon black, graphite, graphene, carbon nanotubes, silver nanoparticles, silver nanowires. Second, inherently conductive polymers may be used. Third, piezoelectric polymers may be used.

Resistive sensors may also be applied at joints. Bending of the joint will stretch the sensor, causing a measurable change in resistance. Pronation and supination of the wrist can be measured by using sensors in the form of long elastic bands that stretch at an angle from the wrist to the elbow. Each motion (e.g. pronation and supination) will create opposite effects in the bands, causing one to lengthen and the other to shorten.

In a fourth sensor aspect, resonant bend sensors may be used. Resonant bend sensors comprise RLC circuits that change resonance frequency when one of the three components changes its value. Rather than having a separate circuit to measure the resistance of each resistive sensor element, the resistive sensors may be wired in parallel at appropriate locations in the neural sleeve. Each sensor may have a different resistance to produce a different resonant frequency in the circuit. A sweep of voltage or current may be used to test each sensor in rapid succession; this measures changes in resonant frequency to determine changes in resistance and thus in strain of that specific sensor.

In a fifth sensor aspect, a sensor may comprise numerous trapped volumes (e.g. fluid bladders) containing air or liquid that respond to changes in motion. For each motion to be detected, a fluid bladder of a specifically designed shape would be placed at an appropriate location such that the pressure in the bladder would change only in response to that motion. For example, there may be one bladder at the wrist in a position and shape to detect wrist flexion, while a different bladder at the wrist detects pronation. Sensing elements, such as pressure transducers or strain gauges, would respond to the pressure changes.

In a sixth sensor aspect, bend sensors also can be made from fiber optics rather than electrical components. The principle is similar to the electronic bend sensors in that when the fiber is bent, a measurable property such as frequency or attenuation changes and this change can be measured. The usage would be similar to the bend sensors described above, with fiber optic bend sensors integrated into the sleeve at joints such as the wrist, such that the sensor bends with bending of the joint.

In a seventh sensor aspect, a variety of video motion tracking systems may be used to measure and track the position of the limb while using the neural sleeve. These systems are similar to the ones used for motion capture in movies and video games. One or more cameras may focus on the sleeve during use. To provide the best accuracy, these systems would include markers at key locations on the sleeve to be tracked. Depending on the type of marker selected, the camera may operate in visible light or infrared. A number of options are available for markers, including: (i) dots in a contrasting color or multiple distinct colors that can be tracked by the external camera(s) (similar to typical movie motion capture); (ii) colored light emitting diodes (LEDs); (iii) Infrared (IR) LEDs at various frequencies in the near-IR range; and (iv) thermal elements such as electrically resistive heaters that create localized warm spots to be tracked by a camera sensitive to long wavelength infrared (LWIR).

Figure 29:
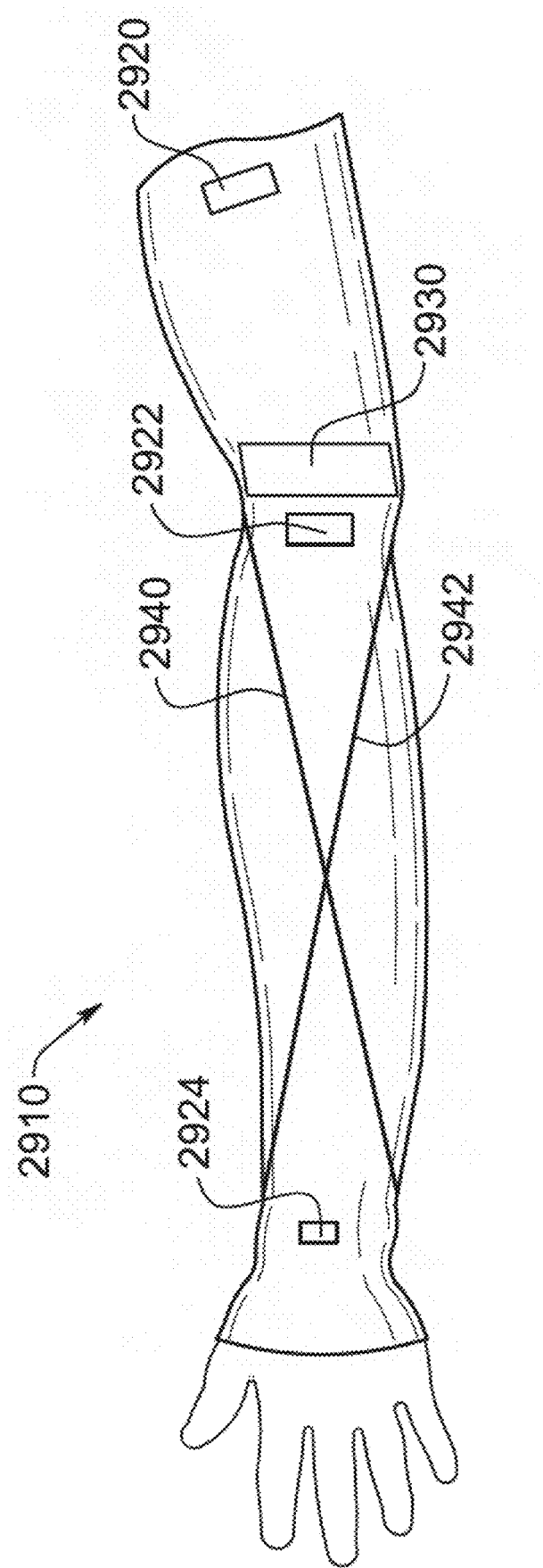
FIG. 29 is an illustrative diagram showing a neural sleeve applied to the arm of a user. This particular neural sleeve is in the form of a fingerless glove that covers the palm of the hand, extends past the wrist and the through the elbow up to the shoulder of the user. The locations of various sensors are highlighted in this diagram.

FIG. 29 is a perspective illustration of a neural sleeve 2910 showing how various sensors could be placed thereon and implemented. The neural sleeve extends from the shoulder down to the wrist. First, a trio of MEMS sensors 2920, 2922, 2924 are located at the shoulder, elbow, and wrist, respectively. These can be used to measure position and orientation relative to each other. Next, a capacitive sensor 2930 is located at the elbow. Resistive bend sensors 2940, 2942 stretch at an angle from the wrist to the elbow. Motion will create opposite effects in these sensors, causing one to lengthen and the other to shorten.

As discussed above, it is contemplated that the neural sleeve will be made of a reusable outer component and an inner component that can be easily disposed of. The inner component comprises a conductive medium that contacts the electrodes present in the outer component and provides a conductive interface/medium between the electrode and the user's skin.

In particular embodiments, the conductive medium can be a hydrogel, or a lotion, or a conductive polymer. In some embodiments, the conductive medium is more conductive in a z-direction and less conductive in either of a x-direction or a y-direction. Put another way, the conductive medium may become more conductive upon application of external pressure, in the direction of external pressure. This property can be obtained from a compressible polymer and a conductive filler dispersed in the compressible polymer. The conductive filler can be in the form of carbon fibers, carbon nanotubes, or metallic particles such as silver, gold, platinum, or palladium. The conductive filler is sparsely distributed in the polymer so that when pressure is applied, the conductive fillers make contact with each other and provide a conductive path from the electrode to the skin. Other conductive hydrogels include a cross-linked alginate polymer or a cross-linked polymeric hydrogel.

In alternative embodiments, to facilitate attachment to a patient, the conductive medium may be selected such that it becomes more tacky or sticky upon application of an electrical current, a change in temperature, a change in pH, or a change in moisture. The conductive medium may be a stimuli-sensitive polymer. To further facilitate attachment and/or delivery of electrical simulation, the electrodes may include concentric rows of teeth about 200 µm to about 300 µm in height.

If desired, the neural sleeve may be configured for gesture control of various devices. Examples of devices that may be controlled are: a computer cursor; an automatic remote; and a haptic interface. The gesture control aspects are also used in virtual reality applications. Gesture control is facilitated by the addition of sensors on the neuromuscular stimulation device/neural sleeve. It is noted that the electrodes present in the neural sleeve for stimulation can also be used for sensing.

In another aspect, a neural sleeve device is used to support gait-training. To facilitate this, the neural sleeve would be adapted to cover both a leg portion and a foot portion of the patient. This allows the neural sleeve to cover both the muscles and the joint of a patient, and advantageously allows for sensing of a foot flexing. A hip portion may also be covered; this allows for stimulation of additional areas to promote recovery following surgery.

In yet another aspect, neuromuscular stimulation may be delivered to the backside of the patient. To facilitate this, the neuromuscular stimulation device may be in the form of a shirt, vest, garment, belt, or so forth, with the electrodes appropriately placed to contact the backside.

The neuromuscular sleeve/neural sleeve could be operated in a wireless, battery-operated mode. In this case, the battery pack and the electronics module can be strapped on the upper arm of the subject in the form of an arm band. The device can be connected to the user's mobile device and/or PC for data transfer and real time tracking/monitoring.

It will further be appreciated that the disclosed techniques may be embodied as a non-transitory storage medium storing instructions readable and executable by a computer, (microprocessor or microcontroller of an) embedded system, or various combinations thereof. The non-transitory storage medium may, for example, comprise a hard disk drive, RAID or the like of a computer; an electronic, magnetic, optical, or other memory of an embedded system, or so forth.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A device for neuromuscular stimulation or electromyography, comprising:
    a compression sleeve comprising a stretchy fabric material configured to be worn on an associated human limb;
    multiple electrodes housed within the compression sleeve and arranged to electrically contact skin of the associated human limb when the compression sleeve is worn on the associated human limb; and
    an inner disposable sleeve surrounded by the compression sleeve, the inner disposable sleeve comprising a conductive medium in contact with the multiple electrodes, wherein the conductive medium comprises a hydrogel which is relatively more conductive in a z-direction than in a x-direction or a y-direction.

2. The device of claim 1, wherein:
    the conductive medium is less conductive in a regular state; and
    the conductive medium becomes more conductive upon application of external pressure along the z-direction in the z-direction of the external pressure.

3. The device of claim 2, wherein the conductive medium comprises a compressible polymer and a conductive filler dispersed in the compressible polymer.

4. The device of claim 3, wherein the conductive filler comprises carbon fibers, carbon nanotubes, or metallic particles.

5. The device of claim 1, further comprising a pulse generator configured to apply a neurostimulation waveform to the electrodes of the compression sleeve.

* * * * *